United States Patent
Öhrlein et al.

(10) Patent No.: US 7,947,848 B2
(45) Date of Patent: May 24, 2011

(54) COLOURED SILSESQUIOXANES

(75) Inventors: Reinhold Öhrlein, Rheinfelden-Herten (DE); Gabriele Baisch, Binzen (DE)

(73) Assignee: BASF SE, Ludwigshafen (DE)

( * ) Notice: Subject to any disclaimer, the term of this patent is extended or adjusted under 35 U.S.C. 154(b) by 194 days.

(21) Appl. No.: 12/308,044

(22) PCT Filed: Jun. 8, 2007

(86) PCT No.: PCT/EP2007/055639
§ 371 (c)(1),
(2), (4) Date: Dec. 4, 2008

(87) PCT Pub. No.: WO2007/147742
PCT Pub. Date: Dec. 27, 2007

(65) Prior Publication Data
US 2009/0203931 A1    Aug. 13, 2009

(30) Foreign Application Priority Data
Jun. 19, 2006  (EP) ..................... 06115663

(51) Int. Cl.
*C07F 7/00*  (2006.01)
(52) U.S. Cl. ........................ 556/460; 556/461
(58) Field of Classification Search .................. 556/460, 556/461
See application file for complete search history.

(56) References Cited

U.S. PATENT DOCUMENTS

| | | | | |
|---|---|---|---|---|
| 5,047,492 | A | 9/1991 | Weidner et al. | 528/15 |
| 5,442,025 | A | 8/1995 | Spes et al. | 528/15 |
| 6,277,451 | B1 * | 8/2001 | Mehl et al. | 428/1.1 |
| 2005/0090015 | A1 | 4/2005 | Hartmann-Thompson | 436/166 |
| 2005/0203227 | A1 | 9/2005 | Kuhnle et al. | 524/261 |
| 2008/0029739 | A1 | 2/2008 | Jeganathan et al. | 252/301.35 |

FOREIGN PATENT DOCUMENTS

| | | |
|---|---|---|
| JP | 2004-196958 | 7/2004 |
| WO | 2005/037955 | 4/2005 |

OTHER PUBLICATIONS

Fujiwara et al., Adv. Funct. Mater., vol. 13, No. 5, (May 2003), pp. 371-376.*
Somlai et al., Mat. Res. Soc. Symp. Proc., vol. 788, (2004), pp. L9.10.1-L9.10.6.*
Mehl et al., Applied Organometallic Chemistry, vol. 13, (1999), pp. 261-272.*
Patent Abstracts of Japan Publication No. 2004196958, Jul. 15, 2004.
A. Somlai et al., Mat. Res. Soc. Symp. Proc., vol. 788, (2004), pp. L9.10.1-L9.10.6.
M. Fujiwara et al., Adv. Funct. Mater., vol. 13, No. 5, (May 2003), pp. 371-376.
G. Mehl et al., Applied Organometallic Chemistry, vol. 13, (1999), pp. 261-272.
Y.-J. Lee et al., Polymer, vol. 47, (2006), pp. 4378-4386.
I. Imae et al., Proc. of SPIE, vol. 5937, (2005), pp. 59371N/1-59371N/8.
I. Imae et al., J. Mater. Chem., vol. 15, (2005)p. 4581-4583.
K. Constantopoulos et al., Polymer Preprints, vol. 45, No. 1, (2004), pp. 668-669.
D. Neumann et al., Journal of the American Chemical Society, vol. 124, No. 47, (2002), pp. 13998-13999.

* cited by examiner

*Primary Examiner* — Porfirio Nazario Gonzalez
(74) *Attorney, Agent, or Firm* — Shiela A. Loggins

(57) ABSTRACT

The invention relates tp dye-functionalized silsesquioxane clusters, a process for their manufacture and their use as colorants, wherein the compounds (functionalized clusters or nano-particles) are characterized by the general formula (I) wherein CAGE is a moiety of the formula (IA) D is a chromophoric moiety, and the other symbols have the meanings as defined in the specification, or salts thereof.

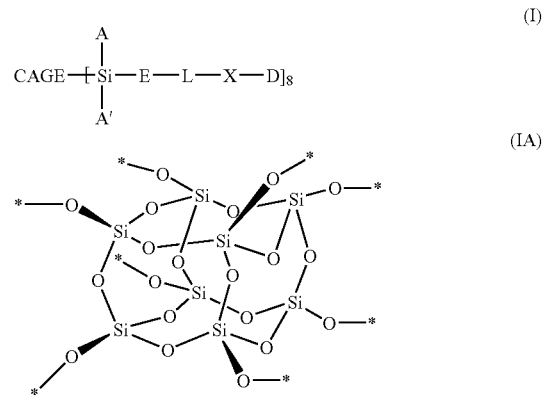

12 Claims, No Drawings

COLOURED SILSESQUIOXANES

SUMMARY OF THE INVENTION

The present invention relates to a new class of colored silsesquisiloxanes, processes for their preparation and their use (as such or as component in a composition) e.g. as colorants, pigments, dyes and the like for coloring of various substrates.

BACKGROUND OF THE INVENTION

Organosilsesquioxanes have been described e.g. in a number of papers and patents (e.g. U.S. Pat. No. 5,047,492).

They can, for example, be used as nano-fillers, nano-composite materials, photoresist material, dendrimers and co-monomers in hybrid materials (M. Fujiwara et al. Advanced Functional Mater. 13, 371 (2003)).

A number of silsesquioxane precursors and various functionalized derivatives are commercially available (Aldrich). The applied hydrosilylation reaction has been described for silsesquioxanes with simple molecules, which do not carry highly functionalized groups and which are used in excess. However, this technology seems to be sensitive to the applied chemicals and is therefore not generally applicable to all alkylene derivatives.

Spherical silica-clusters based on silsesquioxanes are highly thermostable and are claimed to be useful as nano-fillers to improve e.g. the extension modulus of organic polymers or the scratch resistance of coatings (US 2005/203227). U.S. Pat. No. 5,047,492 describes a way of hydrosilylation to produce derivatives of sesquisiloxanes. In other cases (e.g. U.S. Pat. No. 5,442,025; A. P. Somlai et al., Mat. Res. Soc. Symp. Proc. Vol. 788, L9.10 (2004); G. H. Mehl et al., Appl. Organometal. Ch. 13, 261 (1999)) derivatives with mesogenic groups are described (e.g. for Liquid Crystal Displays).

WO 2005/037955 describes light emitting compositions useful for OLEDs where at least two different fluorophores are attached per silsesquioxane molecule as otherwise quenching would take place, and US 2005/090015 describes silsesquioxanes modified to be useful for chemical vapor sensing.

An aim of the present invention is to provide further uses for the class of silsesquioxanes.

GENERAL DESCRIPTION OF THE INVENTION

It has now been found that a new class of silsesquioxane derivatives is useful as colorant in various applications.

It has further been found that, surprisingly, appropriately functionalized dyes, especially polar dyes, can be coupled to silsesquioxanes as is described herein and that this leads to useful coloring agents. The soluble, novel compounds can be used as colorants in various fields, e.g. for materials, goods, formulations, hair, nails, skin or the like (together also referred to as substrates hereinafter).

The compounds (also called clusters) of the invention, described below, bring into said materials an additional effect: coloration. In addition, sensitive dyes and colorants are stabilized by the attachment to the spherical silica cluster, which extends their technical usefulness.

DETAILED DESCRIPTION OF THE INVENTION

The present invention therefore relates, in a first aspect, to novel colored compounds (dye-functionalized silsesquioxane clusters), their process of preparation and their use as colorants, wherein the compounds (functionalized clusters or nano-particles) are characterized by the general formula (I)

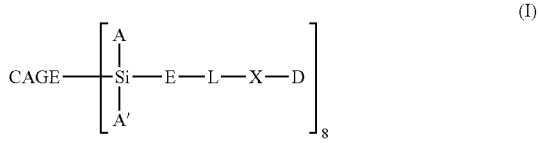

wherein
each of A and A' is, independently of the other, $C_1$-$C_4$ alkyl;
CAGE is a moiety of the formula IA (IA)

[structure shown]

wherein the asterisks (*) mark the bonds binding the moieties of the formula, $$\begin{array}{c} A \\ | \\ -\!\!\!-\mathrm{Si}-\mathrm{E}-\mathrm{L}-\mathrm{X}-\mathrm{D} \\ | \\ A' \end{array}$$

shown above, respectively,
D is a chromophoric moiety, with the proviso that all 8 moieties D in a molecule of the formula I are identical;
E is —$C(R_{3a})(R_3)$—$C(H)(R_{3b})$— and/or

[structure shown with $R_{3b}$, $R_3$, $R_{3a}$, CH]

wherein the double asterisks (**) mark the binding bonds, respectively, and wherein each of $R_3$, $R_{3a}$ and $R_{3b}$, independently of the others, is hydrogen or unsubstituted or substituted $C_1$-$C_{12}$alkyl;
L is unsubstituted or substituted $C_1$-$C_{25}$alkylene which is linear or branched (one or more times), which alkylene may be bound and/or be interrupted by at least one of the radicals selected from the group consisting of —O—, —S—, —N($R_4$)—, —CO—, —O—CO—, —CO—O—, —N($R_4$)—CO—, —CO—N($R_4$)— and phenylene, wherein $R_4$ is hydrogen or unsubstituted or substituted $C_1$-$C_{12}$alkyl;
X is —$NR_5$— or —O—; and
$R_5$ is hydrogen or unsubstituted or substituted $C_1$-$C_{12}$alkyl;
or a salt thereof.

A second embodiment of the invention relates to a method for the manufacture of a compound of the formula I, or a salt thereof, comprising reacting a compound of the formula II,

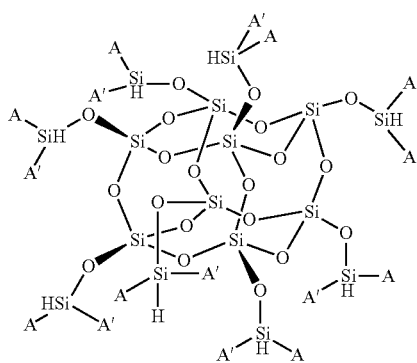

(II)

wherein A and A' are as defined for a compound of the formula I in claim 1 or any one of claims 2 to 8,
under hydrosilylation conditions with a dye compound of the formula III,

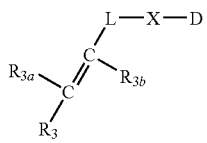

(III)

wherein $R_3$, $R_{3a}$, $R_{3b}$, L, X and D are as defined for a compound of the formula I in claim 1 or any one of claims 2 to 8;
wherein functional groups may be protected;
subsequently removing protecting groups;
and, if desired, converting an obtainable free compound of the formula I into a salt, and/or an obtainable salt of a compound of the formula I into the free compound or into a different salt thereof; and/or separating an obtainable isomer of a compound of the formula I from another obtainable isomer of a compound of the formula I.

Under the hydrosilylation conditions, appropriately functionalized soluble dye precursors of the formula III are reacted with hydrido-compounds of the formula II in the presence of a catalyst, preferably a catalytic amount of a metal catalyst in an organic solvent. The catalysts applied for the hydrosilylation may be selected from one or more from the group consisting of platinum halides, for example $PtCl_4$ or hexa chloro platinic acid $H_2PtCl_6.(H_2O)_x$ (Speier's catalyst), $PtO_2$ on charcoal, 'Karstedt's catalyst, platinum-divinyl tetramethyl-disiloxane complex and many others e.g. given in U.S. Pat. No. 5,831,080 and very recently given by K. Yamamoto et al. Hydrosilylations: hydrosilylation of olefins. Transition Metals for Organic Synthesis (2nd Edition) (2004), 267-181), however preferably platinum catalysts and most preferably soluble platinum catalysts like $H_2PtCl_6.(H_2O)_x$. The amount of catalyst applied may, for example, vary between 1 to 1000, e.g. 2-200 ppm (by weight), preferably 2-50 ppm referring to the amount of platinum contents calculated and the reagent of the formula II or III.

The reaction may be performed without solvent, however, preferably in an organic solvent or solvent mixture, selected e.g. from aliphatic or aromatic hydrocarbons, halogenated solvents, open chain or cyclic ethers or esters, and alcohols, and mixtures thereof, preferably aromatic hydrocarbons, alcohols and ethers, and most preferably solvents like toluene, iso-propanol, dioxane or tetrahydrofuran.

The reaction temperature may vary between 0° C. and reflux temperature of the used solvent, preferably between room temperature and reflux temperature.

Surprisingly, if a sufficient appropriate molar excess (e.g. the 8-fold molar amount or more) of the compound of the formula III over that of the formula II is used, all eight silicium bonded hydrogen atoms in the compound of the formula II take part in the hydrosilylation with the dye derivatives of the formula III.

The hydrosilylation may lead to constitution isomers regarding the place of binding to the double bond (on E) to which the silicon and the hydrogen are attached, however, that does not decisively influence the desired properties of the claimed compounds and therefore only one isomer is represented in the examples below. Usually, however, only the terminal or sterically less hindered carbon carrying both $R_3$ and $R_{3a}$ in formula III is attached to the silicon atom instead of the hydrogen in the compound of formula II.

The proviso that all 8 moieties D in a molecule of the formula I are identical especially means that these moieties are, in a given molecule of the formula I, identical, while for example the binding moiety -E-L- may due to different binding at the double bond of a starting material (see formula III below) vary within one molecule. However, the term "a compound of the formula I" may also include mixtures of two or more such types of molecules with different moieties D where each molecule as such fulfills the proviso that the 8 moieties D in it are identical.

In some methods of preparation for compounds of the formula I or salts thereof and for starting materials as well as in other processes mentioned above and below, functional groups that are not to participate in the respective reaction and which would disturb the desired reaction or lead to side reactions are protected, where required. The introduction and the removal of protection, each at an appropriate stage, follows standard procedures known in the art, e.g. as mentioned in T. W. Greene and P. G. Wuts, "Protective Groups in Organic Synthesis", 3$^{rd}$ edition, John Wiley & Sons, Inc., New York 1999, from which also appropriate protecting groups e.g. for amino, hydroxyl, carboxy or other groups can be deduced conveniently.

Isomeric mixtures of a compound of the formula I as well as of starting materials can be separated into their corresponding isomers in a manner known per se by means of suitable separation methods. The constitution isomers may, for example, be separated by chromatography.

Salts of a compound of formula I with a salt-forming group may be prepared in a manner known per se from the free compound. For example, acid addition salts of compounds of formula I e.g. with basic groups, e.g. amino or imino groups, may be obtained by treatment of the free compound with an acid or with a suitable anion exchange reagent. Salts of a compound of the formula I can usually be converted to free compounds, e.g. by treating with suitable basic agents, for example with alkali metal carbonates, hydrogencarbonates, or hydroxides, typically potassium carbonate or sodium hydroxide. Salts of a compound of the formula I may also be converted into different salts by treatment with appropriate salts. e.g. using a molar excess thereof over the salt of a compound of the formula I.

In yet a further embodiment, the invention also relates to the use of a compound of the formula I, and/or a salt thereof, or a mixture of such compounds and/or salts, or compositions comprising one of more compounds of the formula I and/or salts thereof, as colorant of substrates, for example by applying a compound of the formula I, or a salt thereof, to the outer surface, the inner surface and/or the bulk material of a substrate.

The application can take place by admixing to starting components (e.g. resins or granules for plastics materials or products) or compositions, by coating, and/or by impregnation, and it can take place by using the compounds of the formula I as such or as compositions further comprising other customary additives, such as solvents, binders, preservatives, flavoring agents and the like, wherever appropriate and expedient. In such compositions, a compound of the formula I can, for example, be present in an amount of 0.1 to 90% by weight.

Unless otherwise indicated, the general terms and names used in the disclosure of the present invention preferably have the following meanings (where more specific definitions, in each case separately, or in combination, may be used to replace more general terms in order to define more preferred embodiments of the invention, also in the claims):

The term "lower" or "$C_1$-$C_7$-" defines a moiety with up to and including maximally 7, especially up to and including maximally 4, carbon atoms, said moiety being branched or straight-chained. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tertbutyl.

Where compounds or a compound (especially of formula I) is mentioned herein, this is (if not explicitly mentioned otherwise) always intended to mean the free compound and/or a salt thereof, where salt-forming groups are present, and is also intended to comprise solvates of such a compound or salt, e.g. hydrates. Also, even where not especially mentioned, the starting materials can also be used in the form of salts where salt-forming groups are present and the formation of salts does not lead to undesired reactions.

In the compounds of the formula I and any precursors where L is present and is unsubstituted or substituted $C_1$-$C_{25}$-alkylene, L is preferably bound via a C-atom belonging to L to E and not via one of the radicals from the group consisting of —O—, —S—, —N($R_4$)—, —O—CO— and —N($R_4$)(CO)—, as the compound with such heteroatoms directly bound to E is chemically rather difficult, though not totally excluded.

Salts of compounds of formula I are especially acid addition salts (as basic groups, such as nitrogen atoms in amino or imino, salts with bases in the case of acidic (e.g. carboxy, sulfo or phospho) groups or, where several salt-forming groups are present, can also be mixed salts, also with bases, or internal salts. Acid addition salts are formed, for example, from compounds of formula I with inorganic acids, for example hydrohalic acids, such as hydrochloric acid, sulfuric acid or phosphoric acid, or with organic carboxylic, sulfonic, sulfo or phospho acids. Salts of acid groups in a compound of the formula I, such as carboxy, are, for example, salts with suitable bases, such as non-toxic metal salts derived from metals of groups Ia, Ib, IIa and IIb of the Periodic Table of the Elements, for example sodium or potassium salts, or alkaline earth metal salts, for example magnesium or calcium salts, or salts formed with ammonia or organic amines or with quaternary ammonium compounds. Compounds of formula I having both acidic and basic groups can also form internal salts.

Where the term "comprising" is used, this is intended to mean that the component, components, feature or features mentioned or enumerated thereafter may be fulfilled not only alone, but that also one or more other components and/or features (e.g. other additives, other actions) may be present in addition to those specifically mentioned. This is in contrast to the term "containing" or "consisting of" which mean that no other components or features are included except for those specifically mentioned after such an expression and thus denote a complete enumeration/representation of features and/or components. Wherever "comprising" is used, this may (independently of other occurrences) be replaced by the narrower term "consisting of" or (in case of processes or methods) by "containing the step of", where possible and expedient, thus leading to specific and preferred embodiments of the invention.

Colored means that a compound of the formula I absorbs at least more or less selectively within the visible part of the spectrum (wavelengths about 400 to about 800 nm) at preferably one limited wavelength range. The color realized with the eye then corresponds to the respective complementary colour of the absorbed spectral area(s) which results from the rest of the spectrum in the wavelength area between about 400 to about 800 nm.

A chromophoric moiety D is preferably a moiety comprising, preferably consisting of, a dye molecule bound to X, preferably a dye selected from the group consisting of hydroxy anthraquinones or ethers or esters thereof; amino anthraquinones or amino-hydroxy anthraquinones or ethers or esters thereof, respectively, mercapto-anthraquinones; dyes with anthraquinone nucleus condensed with one or more carbocyclic rings, such as benzanthrones, perylene derivatives, dibenzanthrones, isodibenzanthrones, pyranthrones, dibenzopyrenequinones, benzanthraquinones, Anthanthrones, benzo-, naphtho-, or anthradianthrones, other dyes in which the anthracene nucleus is condensed with one or more carbocyclic rings; dyes with an anthracene nucleus condensed with one or more heterocyclic rings with or without carbocyclic rings, such as pyrazolanthrones, benzanthronylpyrazolanthrone condensation products, dipyrazolanthrones, isothiazolanthrones, isoxazolanthrones, isoselenazolanthrones, thiophenanthrones, benz-azabenzanthrones (anthrapyridones), benz-diazabenzanthrones, e.g. anthrapyrimidones, coeroxenes, coerthienes, coeramidenes, flavanthrones, carbazoles of the anthracene series, anthrimide carbazoles, 1.2 azoles of the anthracene series, 1.3 azoles of the anthracene series, anthraquinone acridones or thioxanthones, amino acridones, compounds containing acridone and carbazole rings, condensation products of benzanthronyl-amino anthraquinones, pyridino anthraquinones, azines of the anthracene series, para-diazines, bis-anthraquinonediazines (indanthrones), thiazines, oxazines, cyclic imides or amidines of peri-dicarboxylic acids of the anthracene, benzanthrene, or perylene series; anthracene dyes not provided for above; Indigoid dyes, such as bis-indole indigos, indonethionaphthene indigos, other indole-indigos, bis-thionaphthene indigos, other thionaphthene indigos; Esters or estersalts of leuco compounds of vat dyestuffs, e.g. of anthracene dyes or of indigoid dyes; diaryl- or triarylmethane dyes, e.g. derived from diarylmethanes, derived from triarylmethanes, hydroxy derivatives of triarylmethanes in which at least one —OH group is bound to an aryl nucleus, phthaleins, amino derivatives of triarylmethanes without any —OH group bound to an aryl nucleus or containing —OH groups bound to an aryl nucleus, phthaleins containing amino groups, triarylmethane dyes in which at least one of the aromatic nuclei is heterocyclic, pyronines;

acridine, azine, oxazine, or thiazine dyes, e.g. acridine dyes; azine dyes of the benzene series, of the naphthalene series or fluorindine or its derivatives; oxazine dyes, such as bisoxazines prepared from amino quinines; thiazine dyes;

quinoline or polymethine dyes, e.g. methine or polymethine dyes, such as cyanine dyes characterised by the methine chain, e.g. cyanines, isocyanines, pseudocyanines, carbocyanines, polycarbocyanines; or containing an even number of ->CH groups, the polymethine chain being branched, e.g. styryl dyes; or the polymethine chain containing hetero atoms; quinophthalones, hydrazone dyes, triazene dyes;

azo dyes, e.g. preparations in which the azo group is formed in any way other than by diazotising and coupling, such as tartrazines; monoazo dyes prepared by diazotising and coupling; disazo or polyazo dyes of the type A→B→C, A→B→C→D, or the like, prepared by diazotising and coupling; disazo or polyazo dyes of the types A→K←B, A→B→K←C, or the like, prepared by diazotising and coupling; disazo or polyazo dyes of the type A←D→B prepared by diazotising and coupling; azo dyes prepared by coupling the diazotised amine with itself; other azo dyes prepared by diazotising and coupling, azo dyes from other azo compounds, azo dyes containing onium groups, azo dyes not provided for in the preceding groups;

porphines or azaporphines, such as phthalocyanines;

quinacridones;

sulfur dyes e.g. from nitro compounds of the benzene, naphthalene or anthracene series, from amino compounds of the benzene, naphthalene or anthracene series, from azines, oxazines, thiazines, or thiazoles, from urea derivatives, from diphenylamines, indamines, or indophenols or from other compounds;

nitro or nitroso dyes;

quinone imides, such as indamines, indophenols;

azomethine dyes;

azo dyes containing other chromophoric systems, such as azomethine-azo dyes, stilbene-azo dyes, bis- or poly-stilbene-azo dyes, styryl-azo dyes, anthraquinone-azo dyes, phthalocyanine-azo dyes, methine- or polymethine-azo dyes, hydrazone-azo dyes, triazeneazo dyes;

other synthetic dyes of known constitution, such as coumarine dyes, isoindoline dyes, naphtholactam dyes, naphthalimide dyes, phthalimide dyes, perinones, i.e. naphthoylenearyl-imidazoles, benzoxanthene dyes; benzothioxanthene dyes;

dyes of natural origin prepared from natural sources;

and reactive dyes, i.e. dyes which form covalent bonds with the substrates or which polymerise with themselves, especially with the linkage of the reactive group being alternatively specified; with the reactive group directly attached to a heterocyclic ring, the heterocyclic ring being alternatively specified, e.g. to a triazine ring, to a pyridazine ring, to a pyrimidine ring, to a pyrazine ring, to a five-membered ring, to some other heterocyclic ring; with the reactive group not directly attached to a heterocyclic ring; or the reactive group being alternatively specified, the reactive group being an acryloyl group, a quaternised or non-quaternised aminoalkyl carbonyl group, or a (—N)$_n$—CO-A-O—X or (—N)$_n$—CO-A-Hal group, wherein A is an alkylene or alkylidene group, X is hydrogen or an acyl radical of an organic or inorganic acid, Hal is a halogen atom, and n is 0 or 1, the reactive group being a halo-cyclobutyl-carbonyl, halo-cyclobutyl-vinyl-carbonyl, or halo-cyclobutenyl-carbonyl group, the reactive group being an esterified or non-esterified hydroxyalkyl sulfonyl or mercaptoalkyl sulfonyl group, a quaternised or non-quaternised aminoalkyl sulfonyl group, a heterylmercapto alkyl sulfonyl group, a vinyl sulfonyl or a substituted vinyl sulfonyl group, or a thiophene-dioxide group, the reactive group being an esterified or non-esterified hydroxyalkyl sulfonyl amido or hydroxyalkyl amino sulfonyl group, a quaternised or non-quaternised amino alkyl sulfonyl amido group, or a substituted alkyl amino sulfonyl group, or a halogen alkyl sulfonyl amido or halogen alkyl amino sulfonyl group or a vinyl sulfonylamido or a substituted vinyl sulfonamido group, the reactive group being an epoxy or halohydrin group, the reactive group being an ethylenimino or N-acylated ethylenimino group or a —CO—NH—CH$_2$—CH$_2$—X group, wherein X is a halogen atom, a quaternary ammonium group or O-acyl and acyl is derived from an organic or inorganic acid, or a beta-substituted ethylamine group, the reactive group being a N-methylol group or an O-derivative thereof; or with other reactive groups; in each case from one of the following classes: anthracene dyes, azo dyes, e.g. monoazo dyes, disazo or polyazo dyes, nitro dyes, porphines; or azaporphines;

more preferably a radical selected from the group comprising or preferably consisting of an acridine dye, an anthraquinone dye, an azamethine dye; an azo dye, e.g. monoazo, disazo or polyazo dye; a benzodifuranone dye, a coumarin dye, a diketopyrrolopyrrol dye, an oxazine dye, e.g. phenoxazine; a dioxazine dye, a carbonyl dye, e.g. indigoid or alizarine; a methine dye, e.g. a phenylogous methin dye, such as diaryl (e.g. phenyl)-methane or triarylmethane, e.g. phenolphthalein or malachite green, or a polymethine, e.g. pinacyanol or pelargonidine; a polymethine dye, a naphthalimide dye, a naphthoquinone dye, a nitroaryl dye, an oxazine dye, e.g. phenoxazine; a perinone dye, a perylene dye, a phenazine dye, a polyaza-annulene dye, e.g. phthalocyanine; a pyrenequinone dye, a quinacridone dye, a quinoneimine dye, a quinophtalone dye, a thiazine dye, e.g. phenothiazine; a thioxanthene dye, an aryl-carbonium dye and a xanthene dye and more preferably the radical of an anthraquinone, monoazo, disazo, polyazo, phthalocyanine and a dioxazine dye, where each of the dye radicals mentioned hereinbefore may be unsubstituted or substituted by one or more, e.g. one to four, substituents, with the substituents especially selected from the group consisting of $C_1$-$C_{10}$-alkyl, hydroxyl, sulfo (—SO$_2$OH) and/or sulfato (—OSO$_2$—OH)-substituted $C_1$-$C_{10}$-alkyl, $C_1$-$C_{10}$-alkoxy, hydroxyl, sulfo and/or sulfato substituted $C_1$-$C_{10}$-alkoxy, trifluoromethyl, hydroxyl, halogen, especially fluoro, chloro, bromo or iodo, carboxyl (—COOH), sulfo, sulfato, phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, a cationic quaternary ammonium (e.g. of the formula —N(G)$_3^+$ wherein G can have the same or different meanings and is $C_1$-$C_{12}$alkyl which can be interrupted by —O— and can be unsubstituted or substituted by hydroxyl or phenyl and wherein the phenyl radical can be further substituted by $C_1$-$C_8$-alkyl, $C_1$-$C_8$-alkoxy or halogen, or is phenyl that is unsubstituted or substituted by $C_1$-$C_8$-alkyl, $C_1$-$C_8$-alkoxy or halogen; most preferably G is $C_1$-$C_{12}$alkyl) or a cationic phosphonium (especially of the formula —P(G)$_3^+$ wherein G is as just defined) group and phenyl or benzoyl wherein phenyl or benzyol is unsubstituted or substituted in the phenyl ring by at least one of the substituents just mentioned above (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts).

Most preferably, a chromophoric moiety is an unsubstituted or substituted anthraquinone moiety, especially selected from the group of radicals having the following formulae, wherein the "#" sign marks the end of the bond that binds to X in formula I (and in formula III):

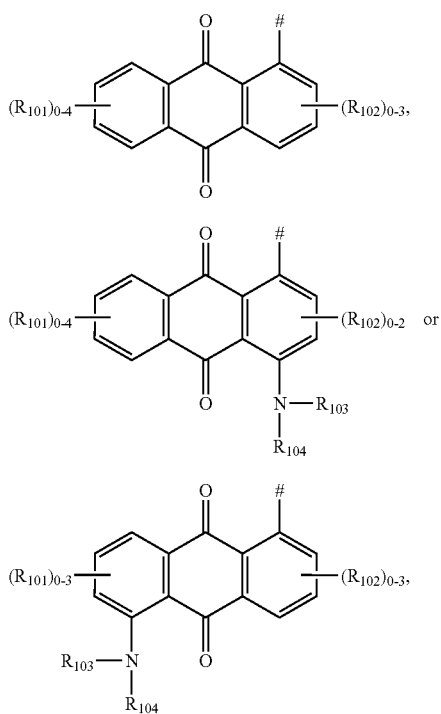

wherein
$R_{101}$ and $R_{102}$ (which may be absent (marked by the zero) or be present up to the given number of times with the index at the lower right) (instead of a hydrogen in the ring to which they are bound) are absent or are substitutents independently of each other selected from $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl, halogen, especially fluoro, chloro, bromo or iodo, carboxyl (—COOH), sulfo (S(O)$_2$OH), sulfato (—O—S(O)$_2$OH), phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, a cationic quaternary ammonium (e.g. of the formula —N(G)$_3^+$ wherein G can have the same or different meanings and is $C_1$-$C_{12}$alkyl which can be interrupted by —O— and can be unsubstituted or substituted by hydroxyl or phenyl and wherein the phenyl radical can be further substituted by $C_1$-$C_8$-alkyl, $C_1$-$C_8$-alkoxy or halogen, or is phenyl that is unsubstituted or substituted by $C_1$-$C_8$-alkyl, $C_1$-$C_8$-alkoxy or halogen; most preferably G is $C_1$-$C_{12}$alkyl) or a cationic phosphonium (especially of the formula —P(G)$_3^+$ wherein G is as just defined) group or phenyl or benzoyl wherein phenyl or benzyol is unsubstituted or substituted in the phenyl ring by at least one of the substituents just mentioned above (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts); and
$R_{103}$ and $R_{104}$ are independently selected from the group consisting of hydrogen, $C_1$-$C_{12}$-alkyl, hydroxyl-substituted $C_1$-$C_{12}$-alkyl, or phenyl or phenyl-$C_1$-$C_{10}$alkyl, in both of which phenyl is unsubstituted or substituted by one or more, especially up to three, moieties independently selected from $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl, halogen, especially fluoro, chloro, bromo or iodo, carboxyl, sulfo, sulfato, phosphono, phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, phenyl or benzoyl wherein phenyl or benzyol is unsubstituted or substituted in the phenyl ring by at least one of the substituents just mentioned (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts); where phenyl or phenyl-$C_1$-$C_{10}$alkyl are preferably substituted by $C_1$-$C_8$alkyl, $C_1$-$C_8$alkoxy, halogen, sulfo, hydroxy or amino; and where it is preferred that at least one of $R_{103}$ and $R_{104}$ is hydrogen.

The index at the lower right of the moieties $R_{101}$, $R_{102}$, $R_{103}$ and $R_{104}$ of the formulae 1a, 1b and 1c mean that zero to two ("0-2"), zero to three ("0-3") or zero to four ("0-4") of said moieties can be present.

In substituted $C_1$-$C_{12}$-alkyl, one or more, especially up to three, substituents are present which, independently of each other, are preferably selected from the group consisting of trifluoromethyl, hydroxyl, halogen, especially fluoro, chloro, bromo or iodo, carboxyl (—COOH), sulfo (S(O)$_2$OH), sulfato (—O—S(O)$_2$OH), phosphono (—P(=O)(OH)$_2$), phospho (—O—P(=O)(OH)$_2$), cyano, nitro, amidino, ureido, carbamoyl, sulfamoyl, amino, $C_1$-$C_{10}$-alkanoylamino, such as acetylamino, mono- or di-($C_1$-$C_{12}$-alkyl)amino, or phenyl or benzoyl wherein phenyl or benzyol is unsubstituted or substituted in the phenyl ring by at least one of the substituents just mentioned (preferably except for substituted phenyl or benzoyl), especially by $C_1$-$C_8$-alkyl, $C_1$-$C_8$-alkoxy, halogen or sulfo; where acidic (e.g. carboxyl, sulfo, sulfato, phosphono, phospho) or basic (e.g. amino, mono- or di-($C_1$-$C_{10}$-alkyl)amino) groups can also be present in anionic or cationic form, respectively (that is, forming salts).

In substituted $C_1$-$C_{25}$-alkylene, which alkylene may be bound and/or be interrupted by at least one of the radicals selected from the group consisting of —O—, —S—, —N(R$_4$)—, —CO—, —O—CO—, —CO—O—, —N(R$_4$)—CO—, —CO—N(R$_4$)— and phenylene, wherein R$_4$ is hydrogen or unsubstituted or substituted $C_1$-$C_{12}$alkyl, one or more, especially up to three, substituents are present, which, independently of each other, are selected from those just mentioned for $C_1$-$C_{25}$-alkyl—the substituents and from unsubstituted or substituted $C_1$-$C_{12}$alkyl R$_4$.

In hydroxyl-substituted (e.g. $C_1$-$C_{12}$) alkyl, one or more hydroxyl groups can be present, preferably one or two.

The soluble, novel compounds can be used as colorants (as such or in the form of compositions with one or more additives)

The term substrates, which can be colored using a compound according to the invention, includes materials, goods, formulations, natural substrates within the living world, such as hair, skin, nails or teeth, or any other tangible things that can be colored by dying and/or pigmenting with the compounds of the formula I.

Materials that can be colored by the compounds of the formula I include for example plastics materials, wood, stone, sand, cement, mortars, resins, coating materials, metals, alloys, textile materials, paper, cardboard, leather, dentine, enamel, or other natural or artificial materials, each of which can be colored on the surface, by impregnation also regarding inner surfaces, or by bulk addition during production or processing where possible, e.g. in the case of plastics, cement, mortars, resins, paper or coating materials. Intermediate materials to obtain final materials or goods are also included. Inorganic materials like silica, alumina, alumo-silica or titano materials can be colored by partial hydrolytic break-up of the claimed clusters in order to incorporate the color-functionalized, now partially opened clusters covalently to said inorganic materials forming organic-inorganic nano-hybrid materials. These materials are useful as optical indicators or detectors e.g. in sensing devices. The colored nano-clusters can be used to produce colored coatings on ceramics or in concrete materials.

Goods can be any finished articles or objects or product parts, such as e-paper, fabrics, cloths, shoes, furniture, vehicles or vehicle components, e.g. tires, print products, electronic products, packaging materials, machines, tools, instruments, music instruments, prosthesis, devices, containers, floor coverings, or the like, including also incomplete products, such as semi-finished products.

Formulations can be therapeutic, diagnostic, cosmetic, fertilizer, dental, cleaning or other homecare compositions which, in addition comprise other customary additives (e.g. solvents, stabilizers etc.) and where present active entities (e.g. pharmaceutically active entities). Other formulations include paints, lacquers, electrostatic toners, inks additives to plastics and polymers, sealants, colorfilters, colored adhesives and/or printing systems.

Natural substrates within the living world can, for example, be hair, nails, skin, teeth, feathers or the like.

In addition, the use of the compounds of the formula I may be for example in packaging, tagging and labeling applications, and the like.

Starting Materials

The invention relates also to novel starting materials, novel methods of manufacture of starting materials and intermediates and novel combinations of method of manufacturing steps, where appropriate and expedient.

The starting materials of the formula II are known or can be prepared according to methods that are known in the art, e.g. by or in analogy to the method described in the Examples.

Starting materials of the formula III are basically the corresponding dye molecule radicals D carrying the group X-L-C($R_{3b}$)=C($R_3$)($R_{3a}$), wherein X, L, $R_3$, $R_{3a}$ and $R_{3b}$ are as defined for a compound of the formula I.

These compounds can be prepared by or in analogy to known methods, are known and/or are commercially available. For example, a fluoride of the formula IV, D-Hal  (IV)

wherein D is as defined for a compound of the formula I and Hal is halogen, preferably fluoro, chloro, bromo or iodo, can be coupled with a compound of the formula V,

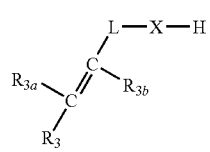

(V)

wherein X, L, $R_3$, $R_{3a}$, and $R_{3b}$ are as defined for a compound of the formula I, for example in the presence of an appropriate base, such as a metal carbonate, e.g. cesium, sodium or potassium carbonate, where useful in the presence of a catalyst, such as 2,2'-bis(diphenylphosphino)-1,1'-binaphthyl and/or Pd(dba)$_2$ (dba=dibenzylidenacetone), in an appropriate solvent, e.g. an ether, such as dioxane, at temperatures e.g. from about 0° C. to the reflux temperature of the reaction mixture, e.g. from 0 to 100° C., resulting in the corresponding compound of the formula III.

Alternatively, a compound of the formula III wherein L is interrupted by a group —K—C(=O)— wherein K is NH or O alone or further a para-phenylene group, the carbonyl group of which is bound to the group ($R_3$)($R_{3a}$)C=C($R_3$)— in formula III, can be obtained from a compound of the formula VI,

(VI)

wherein K is O or NH and L' is a precursor group of a group L (that is, a complementary group that together with Q-C(=O)—O— defined subsequently forms a corresponding moiety L) as defined for a compound of the formula I where the group —O—C(=O) alone or with the further p-phenylene group just mentioned is not yet present but instead the hydroxyl group is present, with an unsaturated acid of the formula VIII,

($R_3$)($R_{3a}$)C=C($R_3$)-Q-COOH  (VII), wherein $R_3$, $R_{3a}$ and $R_{3b}$ are as defined for a compound of the formula I and Q is absent or is p-phenylene, or a reactive derivative thereof, e.g. an ester, an anhydride, a halogenide (e.g. chloride) or an active ester thereof, in an appropriate solvent or solvent mixture, such as toluene or dichloromethane, in the absence or presence of an enzyme, e.g. lipase, such as NOVO 435 (Novozymes, Denmark) and/or an appropriate base, e.g. a tertiary nitrogen base, e.g. at temperatures in the range from −50 to 60° C., if desired under mild vacuum, which reaction results in a compound of the formula III*,

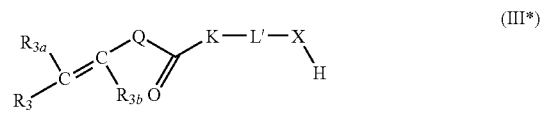

(III*)

wherein $R_3$, $R_{3a}$, $R_{3b}$ and X are as defined for a compound of the formula I and K, Q and L' are as defined for a compound of the formula VI and of the formula VII, respectively, which falls under formula III wherein -Q-C(=O)—K-L' together form (a special variant of) L.

A compound of the formula VI can, for example, be prepared by reacting a compound of the formula VIII,

(VIII)

wherein L' and X are as defined for a compound of the formula VI, with a compound of the formula IV as given above under the same or analogous conditions as described above for the reaction of a compound of the formula IV with a compound of the formula V, in the case where K is NH if required protecting the NH e.g. with a tert-butoxy group and removing the protecting group after the reaction, or in the presence of e.g. copper powder and a base such as sodium acetate or potassium carbonate in toluene at elevated temperatures, e.g. from 30 to 90° C.

Preferably, the compounds of the formula III can be prepared as described in the examples.

PREFERRED EMBODIMENTS OF THE INVENTION

Very important meanings for L are the bridge member of formula —$C_1$-$C_{25}$alkylene-, wherein the $C_1$-$C_{25}$alkylene radical is uninterrupted or bound via or interrupted by at least one of the radicals selected from the group consisting of —N($R_4$)—, —O— or —S— and phenylene, with the proviso that the $C_1$-$C_{25}$alkylene and phenylene may be substituted as given above, or preferably be unsubstituted with the structural exemptions given above.

The invention especially refers to the compounds of the formula I, processes, methods and uses given in the claims, especially in the dependent claims, which are incorporated by reference herein, and especially to the compounds, their manufacture and/or their use given in the Examples.

EXAMPLES

The following examples illustrate the invention without limiting its scope. Parts or percentages are by weight.

The starting materials used in the subsequent Examples can be prepared as follows:

Reference Example A)

Synthesis of a Compound of Formula (1.1)

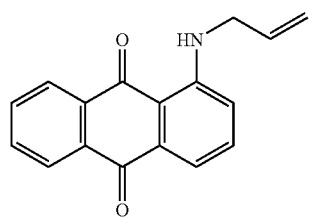

(1.1)

The compound of formula (1.1) is obtained from the corresponding 1-fluoro-anthraquinone (commercially available or prepared according EP 0430434). A mixture of 7.5 g of the fluoro-anthraquinone with 25 ml of allylamine (Fluka) and 4.5 g of potassium carbonate (Fluka) in 150 ml of dioxane is stirred vigourously at 40° C. for about 24 h until all of the starting fluoride is consumed. The reaction mixture is then filtered and the solvent evaporated. The resulting residue is taken up in ethyl acetate and washed successively with 0.1 N hydrogen chloride (2 times), sodium hydrogen carbonate and finally brine. Evaporation of the solvent leaves the pure 1-N-allyl-anthraquinone (1.1) as an amorphous solid: $^1$H-NMR (CDCl$_3$, 300 MHz): δ 3.94 (m, 2H); 5.17 (dq, 1H); 5.27 (dq, 1H); 5.91 (ddt, 1H); 6.96 (dd, 1H); 7.44 (dd, 1H); 7.52 (dd, 1H); 7.61 (dt, 1H); 7.67 (dt, 1H); 8.15 (ddd, 1H); 8.20 (ddd, 1H); 9.77 (broad s, NH). $^{13}$C-NMR (CDCl$_3$, 75 MHz): 644.12; 114.67; 115.46; 116.92; 125.47 (2C); 131.70; 131.80; 132.45; 132.65; 132.82; 133.41; 133.72; 133.93; 150.29; 183.79; 184.00.

Reference Example B)

Synthesis of a Compound of Formula (2.1)

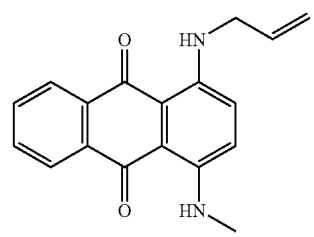

(2.1)

Compound (2.1) is obtained from 1-bromo-4-(N-methylamino)-anthraquinone (prepared e.g. according to: K. S. Chamberlain, Synthetic Commun. 1995, 25, 27). 5.0 g of that bromide, 1.8 ml of allylamine (Fluka), 15.4 g of cesium carbonate (Fluka), 0.78 g BINAP (Aldrich) and 0.10 g of Pd(dba)$_2$ (Aldrich) are heated in 100 ml of dry dioxane under a nitrogen atmosphere to 100° C. for 4 h until all of the starting bromide is consumed. The resulting mixture is cooled down, diluted with dichloromethane and washed successively with water and then brine. Evaporation of the solvent leaves a residue which is purified over a silica gel column (Fluka: mesh 230-400) and eluent (hexane-ethyl acetate 15:1 (v/v)) to give the compound of formula (2.1): $^1$H-NMR (CDCl$_3$, 300 MHz): δ 3.00 (d, 3H); 3.97 (m, 2H); 5.14 (dq, 1H); 5.23 (dq, 1H); 5.91 (ddt, 1H); 7.09 (s, 2H); 7.60 (m, 2H); 8.23 (m, 2H); 10.47 (broad s, NH); 10.67 (broad s, NH). $^{13}$C-NMR (CDCl$_3$, 75 MHz): δ 29.77; 45.36; 110.03; 110.25; 116.64; 122.81; 123.71; 126.13; 126.17; 132.02; 132.10; 134.54 (2C); 134.62; 145.79; 146.95; 182.22; 182.56.

Reference Example C)

The known compound of formula (3) (octakis(hydrodimethylsilyloxy)octasilsesquioxane) is synthesized according to the literature protocol (D. Höbbel et al., Z. Chem. 1989, 260) in about 82% from the commercial cage compound (3a) (Aldrich); the structure of (3) is proven by the NMR-data below. Alternatively, (3) can directly be bought from Sigma-Aldrich ("Aldrich"), St. Louis, Mo., USA.

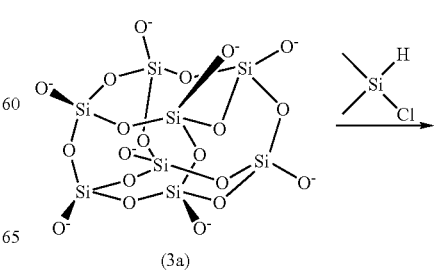

(3a)

-continued

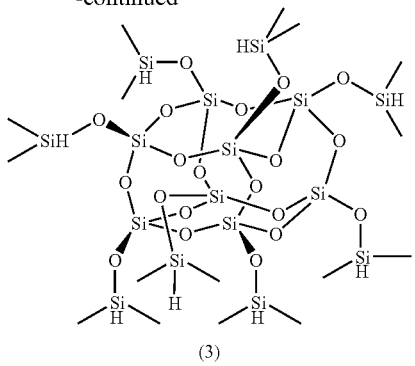

(3)

(counterions not shown in formula (3a))
$^1$H-NMR (CDCl$_3$, 500 MHz): δ 0.20 (s, 6H); 4.75 (s, 1H).
$^{13}$C-NMR (CDCl$_3$, 75 MHz): δ 0.00.
$^{29}$Si-NMR (CDCl$_3$, 99 MHz): δ −108.65; −1.35.

Example 1

Red Cluster Compound (1) Synthesis from (3) and (1.1)

In an argon atmosphere, 7.2 g of compound (3) (Reference Example C)), 19.3 g of anthraquinone compound (1.1) (Reference Example (A)) and 1.0 ml of a solution of hexachloroplatinum acid (0.10 g in 10 ml tetrahydrofuran) are dissolved in 340 ml of dry toluene and heated to 100° C. for 24 h until compound (3) is consumed. The solvent is then evaporated and the residue passed over a short silica gel pad (Fluka: mesh 230-400) and eluent (hexane-ethyl acetate 10:1 (v/v)) to remove unreacted excess anthraquinone. The desired product is then purified over a silica gel column (Fluka: mesh 230-400) and eluent (methanol-dichloro methane 1:10 (v/v)) to give the red cluster compound (1) as a single isomer: $^1$H-NMR (CDCl$_3$, 500 MHz): δ 0.29 (s, 6H); 0.82 (m, 2H); 1.83 (m, 2H); 3.33 (q, 2H); 6.87 (dd, 1H); 7.39 (m, 2H); 7.62 (m, 2H); 8.10 (ddd, 2H); 9.60 (broad t, NH). $^{13}$C-NMR (CDCl$_3$, 75 MHz): δ −1.17; 14.24; 21.90; 44.92; 111.62; 114.51; 116.64; 125.65 (2C); 131.92 (2C); 132.89; 133.44; 133.84; 134.20; 150.44; 182.43; 183.63. $^{29}$Si-NMR (CDCl$_3$, 99 MHz): δ −108.79; 13.13.

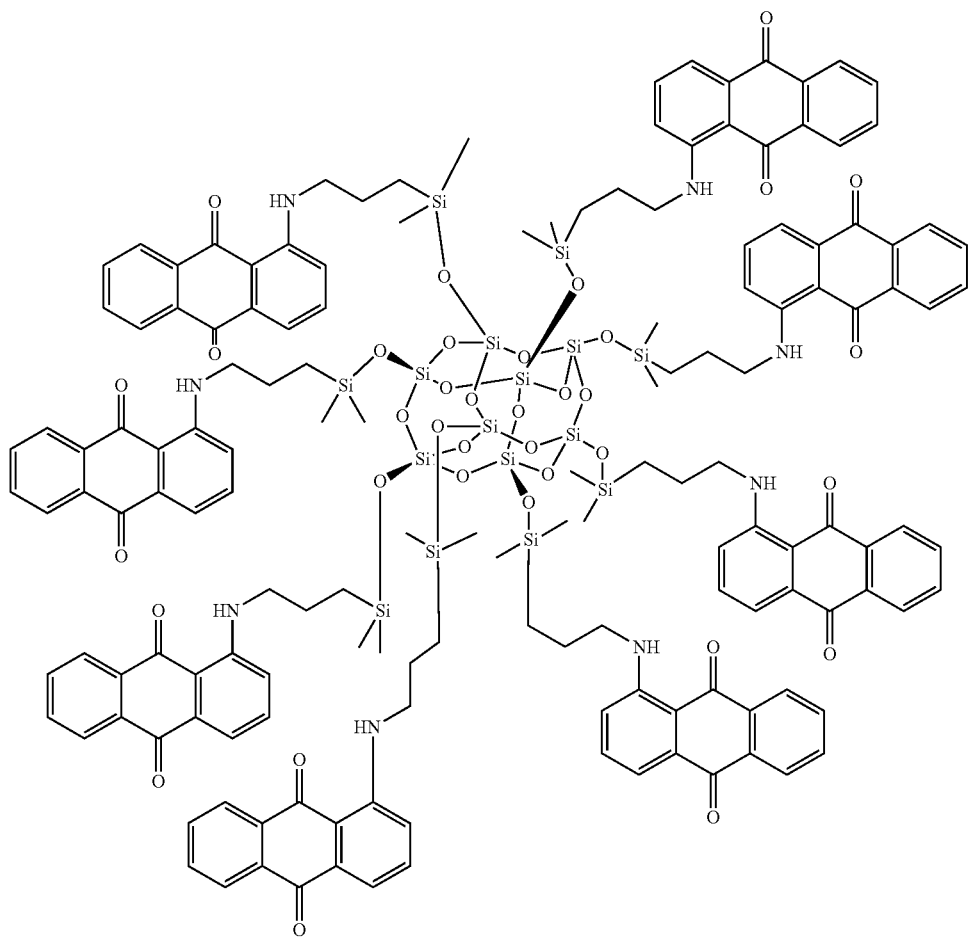

(1)

Example 2

Blue Cluster Compound (2) Synthesis from (3) and (2.1)

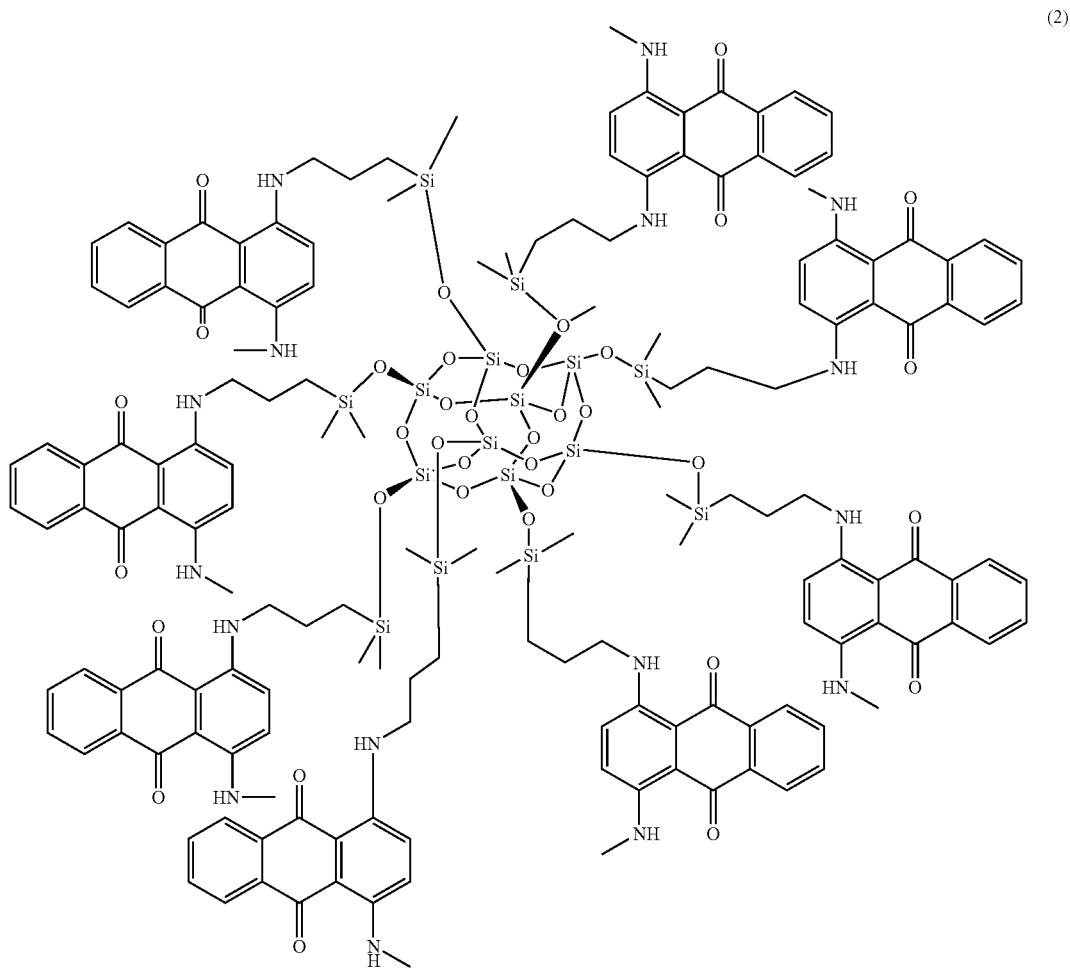

In an argon atmosphere 3.0 g of compound 3, 10.3 g of anthraquinone compound (2.1) (Reference Example (B)) and 0.8 ml of a solution of hexachloroplatinum acid (0.10 g in 10 ml tetrahydrofuran) are dissolved in 150 ml of dry toluene and heated to 100° C. for 24 h until compound (3) is consumed. The solvent is then evaporated and the residue passed over a short silica gel pad (Fluka: mesh 230-400) and eluent (hexane-ethyl acetate 10:3 (v/v)) to remove unreacted excess anthraquinone. The desired product is then purified over a silica gel column (Fluka: mesh 230-400) and eluent (methanol-dichloro methane from 1:3 to 2:3 (v/v)) to give the blue cluster compound (2) as a single isomer: $^1$H-NMR (CDCl$_3$, 500 MHz): δ 0.36 (s, 6H); 0.87 (m, 2H); 1.90 (m, 2H); 2.92 (d, 3H); 3.31 (m, 2H); 6.85 (d, 1H); 6.93 (d, 1H); 7.66 (dd, 2H); 8.27 (dd, 2H); 10.45 (broad q, NH); 10.75 (broad t, NH). $^{13}$C-NMR (CDCl$_3$, 75 MHz): δ 0.00; 15.51; 23.40; 29.32; 46.04; 109.39 (2C); 122.58; 122.96; 125.82 (2C); 131.55 (2C); 134.31 (2C); 146.46 (2C); 181.65 (2C).
$^{29}$Si-NMR (CDCl$_3$, 99 MHz): δ –108.6; 13.15.

The following Examples can be prepared in analogy to those mentioned before:

Formula of the compounds in the following Examples:

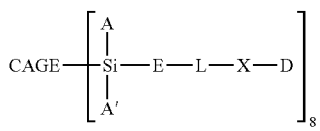

wherein CAGE is as defined for compounds of the formula I and the moieties

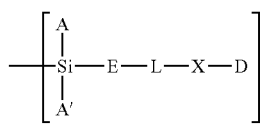

are as defined in the table (the asterisks at the half-bonds mark the place where the bond is formed in a compound of the formula I with the half-bonds in formula IA also marked with an asterisk:

| Example | $*-\underset{\underset{A'}{|}}{\overset{\overset{A}{|}}{Si}}-E-L-X-D$ |
|---|---|
| 3 | 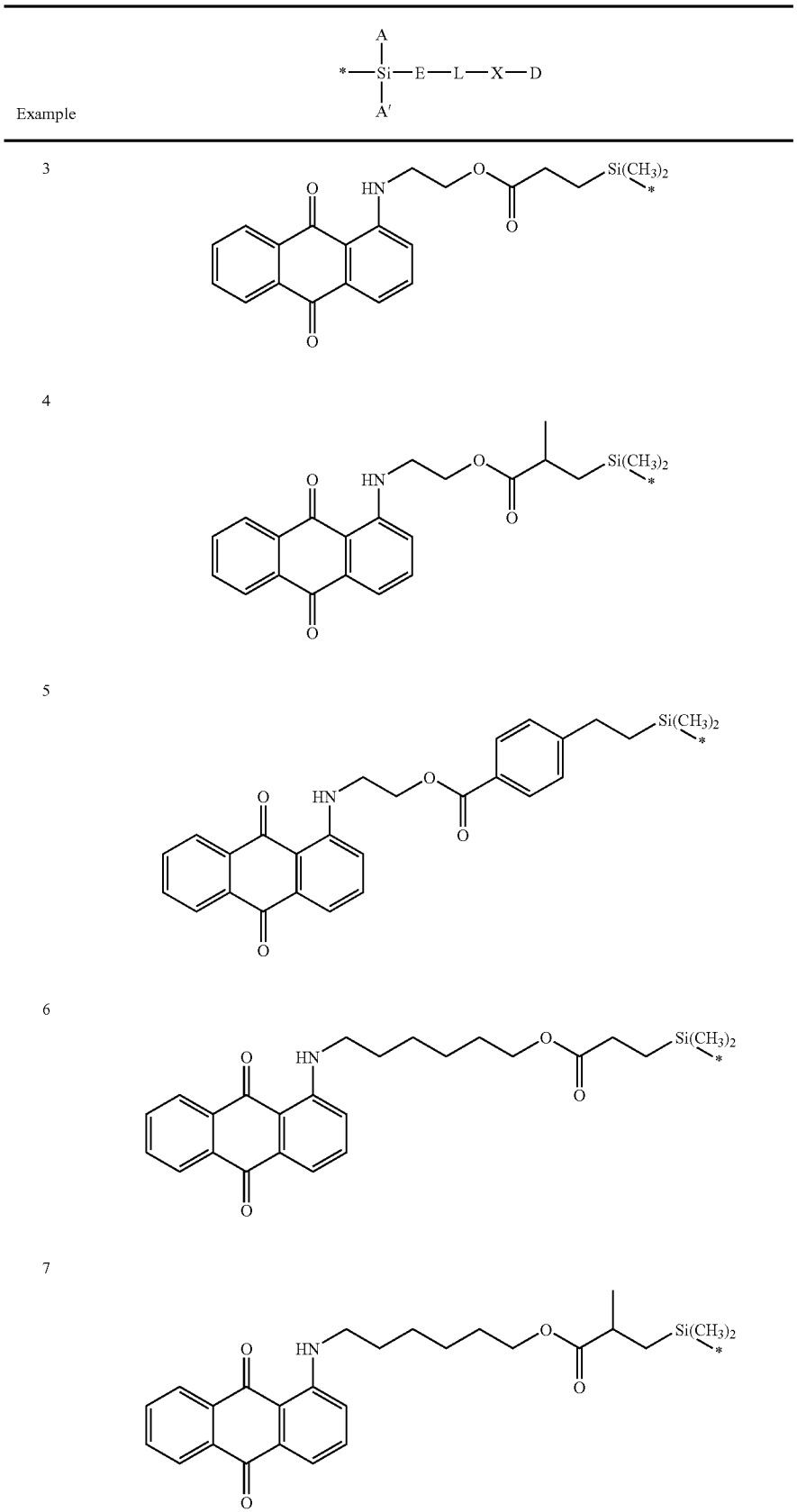 |
| 4 | |
| 5 | |
| 6 | |
| 7 | |

-continued
| Example | 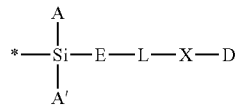 |
|---|---|
| 8 | 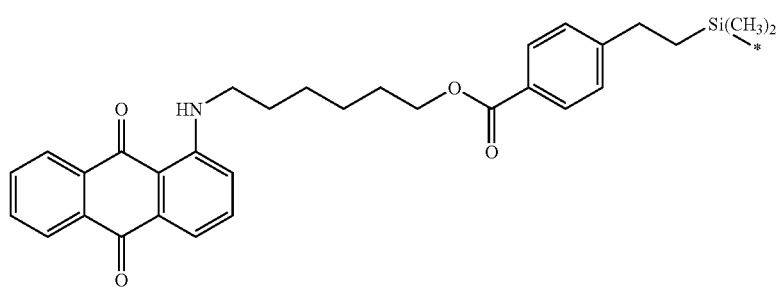 |
| 9 | 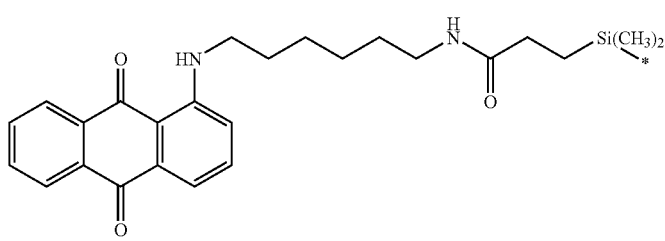 |
| 10 | 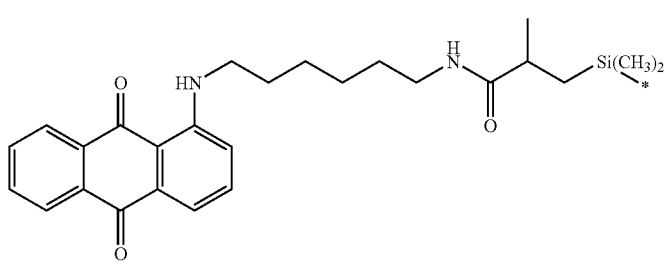 |
| 11 | 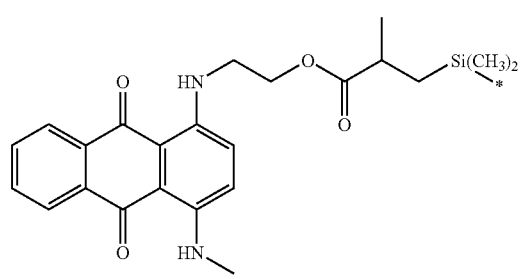 |
| 12 | 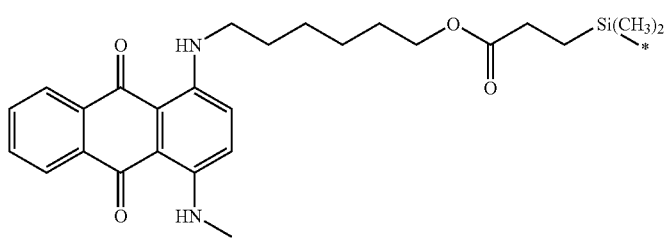 |

| Example | *—Si(A)(A')—E—L—X—D |
|---|---|
| 13 | 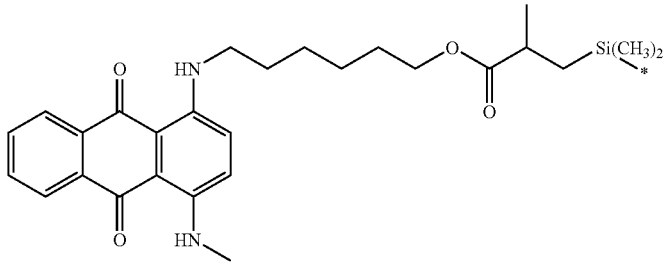 |
| 14 | 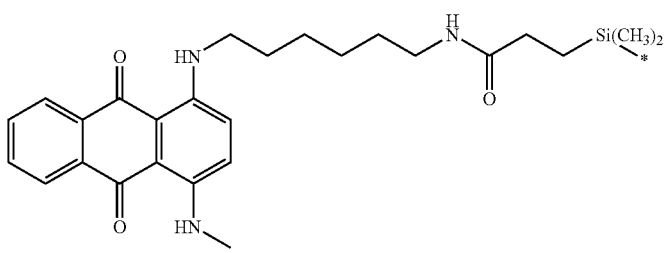 |
| 15 | 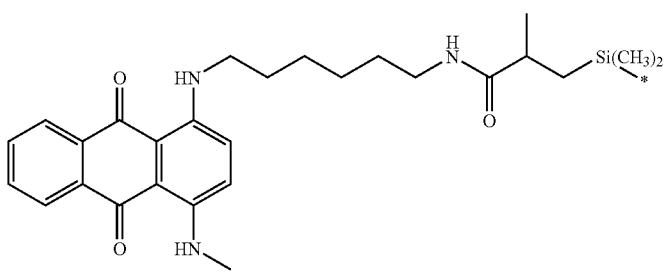 |

The corresponding starting materials of the formula III can be prepared as follows:

For Example 3

Synthesis of the Compound of Formula (3.1)

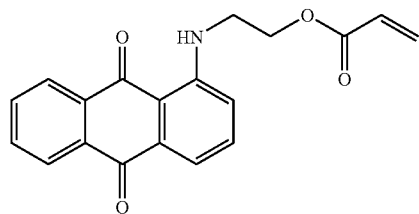

(3.1)

The red compound of formula (3.1) is obtained in analogy to compound 6.1 below from 0.25 g of the compound of formula (3.2) and 1.00 ml acrylic acid methyl ester. $^1$H-NMR (CDCl$_3$, 300 MHz): 3.49 (dt, 2H, 4.31 (t, 2H); 5.76 (dd, 1H); 6.05 (dd, 1H); 6.35 (dd, 1H); 6.90 (dd, 1H); 7.33 (dd, 1H); 7.39 (dd, 1H); 7.54 (m, 2H); 8.04 (m, 2H); 9.67 (broad t, 1H). $^{13}$C-NMR (CDCl$_3$, 75 MHz): 41.85; 62.90; 113.59; 116.19; 117.57; 126.75; 126.84; 128.19; 131.63; 133.04; 133.09; 133.96; 134.75; 134.91; 135.37; 151.37; 166.06; 183.42; 185.00.

Compound 3.2:

The Red Compound 3.2

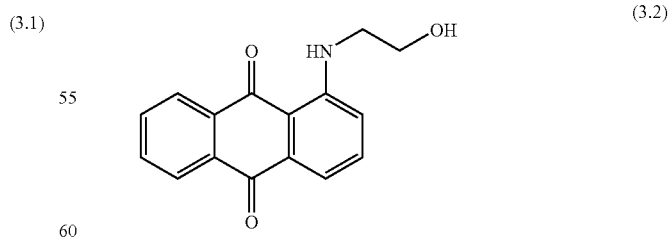

(3.2)

is obtained in analogy to Reference Example A) from 1.50 g of 1-fluoro-anthraquinone and 1.00 ml of ethanolamine. $^1$H-NMR (CDCl$_3$, 300 MHz): 1.65 (s, broad, 2H); 3.47 (t, 2H); 3.90 (t, 2H); 7.01 (dd, 1H); 7.43 (dd, 1H); 7.50 (dd, 1H); 7.57-7.68 (m, 2H); 8.14 (m, 2H); 9.56 (broad t, 1H).

For Example 4

The Compound of Formula 4.1

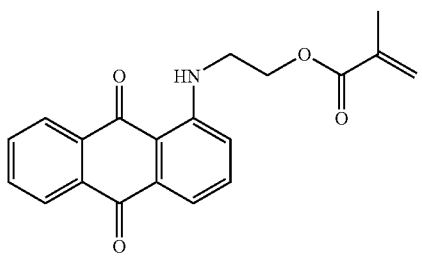

(4.1)

is obtained in analogy to compound 3.1, using methacrylic acid methylester. $^1$H-NMR (CDCl$_3$, 300 MHz): 1.90 (s, 3H); 3.62 (dt, 2H); 4.36 (t, 2H); 5.52 (t, 1H); 6.11 (s, 1H); 7.06 (dd, 1H); 7.50 (m, 2H); 7.65 (m, 2H); 8.17 (m, 2H); 9.83 (broad t, 1H). $^{13}$C-NMR (CDCl$_3$, 75 MHz): 17.24; 40.43; 61.67; 112.32; 114.85; 116.29; 124.99; 125.43; 125.49; 131.72; 132.61; 132.65; 133.50; 133.63; 134.04; 134.67; 136.55; 150.14; 165.91; 182.22; 183.79.

For Example 5

The Compound of the Formula 5.1

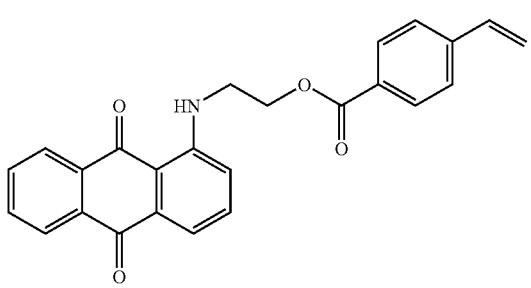

(5.1)

is obtained in analogy to Example 3.1). $^1$H-NMR (C$_6$D$_6$, 300 MHz): 2.79 (dt, 2H); 3.92 (t, 2H); 4.81 (d, 1H); 5.29 (dd, 1H); 6.15 (dd, 1H); 6.32 (dd, 1H); 6.78-6.88 (m, 5H); 7.47 (dd, 1H); 7.87 (m, 2H); 7.96 (m, 2H); 9.78 (broad t, 1H).

For Example 6

The Compound of the Formula 6.1

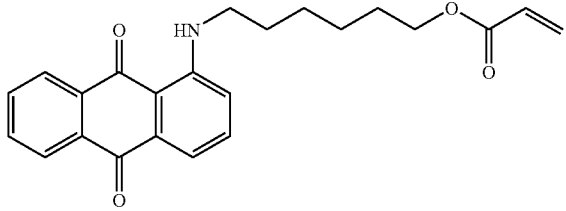

(6.1)

is obtained as follows: The compound of formula (6.2) is esterified in the presence of the biocatalyst NOVO 435 (Novozymes, Denmark). At 50° C. and a vacuum at about 450 mbar 10.0 g of the compound of formula (6.2), 22.2 ml of acrylic acid methyl ester and 5.0 g of the biocatalyst are reacted in 75 ml toluene for 24 hours until all of the starting compound of formula (6.2) is consumed. The mixture is then filtered, washed with dichloromethane and the solvent evaporated. After vacuum drying, the desired red acrylic ester of formula 6.1) is obtained. $^1$H-NMR (CDCl$_3$, 300 MHz): 1.35-1.77 (m, 8H); 3.25 (dt, 2H); 4.10 (t, 2H); 5.73 (dd, 1H); 6.04 (dd, 1H); 6.28 (dd, 1H); 6.96 (dd, 1H); 7.44 (dd, 1H); 7.50 (dd, 1H); 7.60 dt, 1H); 7.66 (dt, 1H); 8.14 (m, 2H); 9.64 (broad, t, 1H). $^{13}$C-NMR (CDCl$_3$, 75 MHz): 26.15; 27.23; 28.93; 29.40; 43.19; 64.77; 113.11; 115.77; 117.98; 126.83; 126.88; 128.78; 130.67; 133.04; 133.22; 134.06; 134.87; 135.22; 135.43; 151.90; 166.40; 183.87; 185.04.

Compound (6.2):

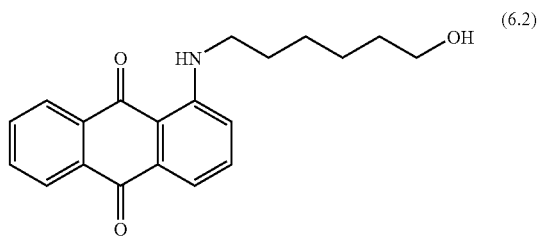

(6.2)

A mixture of 6.0 g of 1-fluoro-anthraquinone, 3.4 g hexanolamine (FLUKA) and 4.0 g potassium carbonate is heated with stirring to 95° C. for 25 hours until the starting fluoride is consumed. The reaction mixture is then filtered and the dioxane evaporated. The red residue is taken up in ethyl acetate and extracted successively with 1 N hydrogen chloride (3 times), saturated sodium hydrogen chloride solution and brine. Evaporation of the solvent leaves a red residue which is purified over a short silica gel column (230-400 mesh, FLUKA) and eluent (hexane-ethyl acetate 10:2 (v/v)) to give the desired red compound of formula (6.2). $^1$H-NMR (CDCl$_3$, 300 MHz): 1.40-1.81 (m, 8H); 3.26 (ddd, 2H); 3.66 (t, 2H); 6.98 (dd, 1H); 7.45 (ddd, 1H); 7.50 (dd, 1H); 7.62-773 (m, 2H); 8.15-8.22 (m, 2H). $^{13}$C-NMR (CDCl$_3$, 75 MHz): 25.85; 27.29; 29.34; 32.79; 43.06; 62.70; 112.94; 115.76; 118.11; 126.78; 126.83; 133.05; 133.13; 134.13; 134.74; 135.18; 135.45; 151.78; 184.06; 184.99.

For Example 7

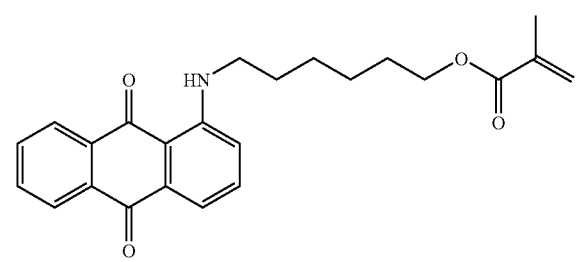

(7.1)

In analogy to the synthesis of compound 6.1, 10.5 g of the ester of formula (7.1) are obtained from 10.0 g of the alcohol of formula (6.2) and 8.0 g of biocatalyst in 60 ml of toluene. $^1$H-NMR (CDCl$_3$, 300 MHz): 1.36-168 (m, 8H); 1.87 (dd, 3H); 3.8 (m, 2H); 4.08 (t, 2H); 5.45 (m, 1H); 6.01 (m, 1H); 6.76 (dd, 1H); 7.23 (ddd, 1H); 7.35 (ddd, 1H); 7.48-7.60 (m, 2H); 8.02 (m, 2H); 9.44 broad t, 1H). $^{13}$C-NMR (CDCl$_3$, 75

MHz): 18.65; 26.14; 27.16; 28.89; 29.90; 40.05; 64.79; 112.95; 115.47; 117.70; 125.31; 126.56; 126.65; 132.77; 132.99; 133.78; 134.50; 134.97; 135.09; 136.59; 151.51; 167.38; 183.31; 184.49.

112.95; 115.72; 117.99; 126.24; 126.76; 126.80; 131.25; 133.01; 133.12; 134.03; 134.71; 135.12; 135.38; M 151.80; 165.77; 183.77; 184.90.

Compound 9.2:

For Example 8

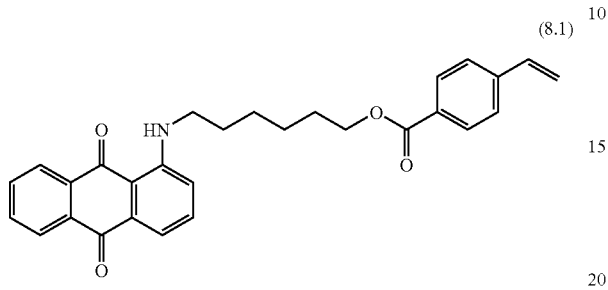
(8.1)

The compound of formula (8.1) is obtained in analogy to Example 6.1. $^1$H-NMR (CDCl$_3$, 300 MHz): 1.20-165 (m, 8H); 3.17 (q, 2H); 4.23 (t, 2H); 2.26 (dd, 1H); 5.73 (dd, 1H); 6.59 (dd, 1H); 6.87 (dd, 1H); 7.28-7.44 (m, 4H); 7.50-7.62 (m, 2H); 7.84 (m, 2H); 8.09 (m, 2H); 9.56 (broad t, 1H). $^{13}$C-NMR (CDCl$_3$, 75 MHz): 24.78; 25.76; 27.57; 27.91; 41.68; 63.67; 111.55; 114.22; 115.15; 116.45; 124.80 (2×C); 125.33 (2×C); 128.27; 128.54 (2×C); 131.48; 131.70; 132.51; 133.27; 133.68; 133.86; 134.71; 140.55; 150.32; 165.00; 182.24; 183.40.

At room temperature, 10.2 g of the Boc-protected compound of formula (9.3) are dissolved in 50 ml of dioxane. To this mixture, then a solution of 50 ml 4 N hydrogen chloride in dioxane is added in small portions with vigorous stirring until the starting compound of formula (9.3) is consumed. The compound of formula (9.2), as its hydrogen chloride salt, is filtered off and successively washed with dioxane, hexane and dichloromethane and finally dried on high vacuum to give a red powder. $^1$H-NMR (CD$_3$OD, 300 MHz): 1.26-1.85 (m, 6H); 2.94 (t, 2H); 3.24 (dt, 2H); 6.96 (dd, 1H); 7.43 (dd, 1H); 7.49 (dd, 1H); 7.60 (dt, 1H); 7.67 (dd, 1H); 8.16 (m, 2H); 9.64 (broad t, 1H). $^{13}$C-NMR (CD$_3$OD, 75 MHz): 27.03; 27.45; 29.48; 34.08; 42.51; 43.27; 113.09; 115.74; 118.03; 126.83; 126.88; 133.03; 133.24; 134.07; 134.89; 135.24; 135.43; 151.95; 183.91; 184.05.

Compound 9.3:

For Example 9

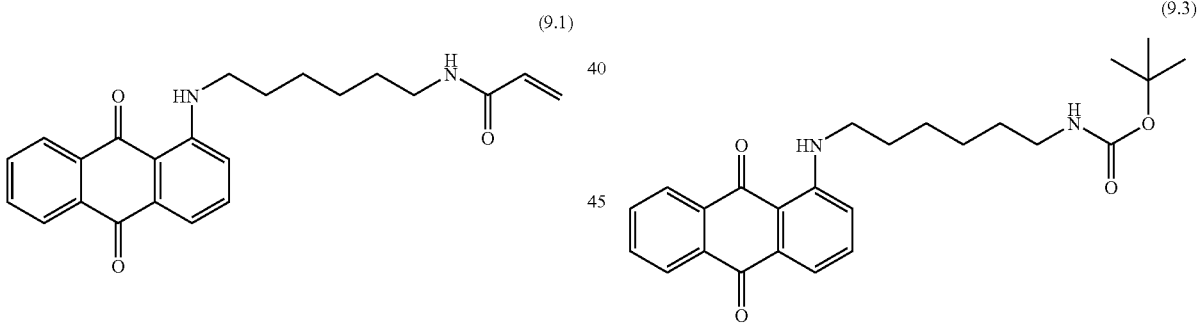

The compound of formula (9.2) (6.50 g) is completely dissolved together with 10.1 ml triethyl amine in 120 ml of dry dichloromethane at room temperature (about one hour) and then cooled down to −40° C. to −50° C. At this temperature, 1.80 ml of acrylic acid chloride dissolved in 50 ml of dichloromethane are added within 45 minutes. Additional dichloromethane (100 ml) is added to the reaction mixture. The organic phase is then successively extracted with 1 N hydrogen chloride (3 times), a solution of saturated sodium hydrogen carbonate and brine. The organic phase is dried over sodium sulphate, filtered and evaporated to give the desired acryl amide of formula (9.1. $^1$H-NMR (CDCl$_3$, 300 MHz): 1.20-1.58 (m, 6H); 1.64-1.74 (m, 2H); 3.19-3.32 (m, 4H); 5.54 (dd, 1H); 5.71 (broad, s, 1H); 6.02 (dd, 1H); 6.18 (dd, 1H); 6.94 (dd, 1H); 7.42 (dd, 1H); 7.47 (dd, 1H); 7.56-7.68 (m, 2H); 8.14 (m, 2H); 9.61 (broad t, 1H). $^{13}$C-NMR (CDCl$_3$, 75 MHz): 27.01; 27.18; 29.29; 29.82; 39.81; 43.11;

A mixture of 6.75 g N-Boc-1,6-diaminohexane (ALFA AESAR), 3.60 g potassium carbonate and 5.80 g of 1-fluoro-anthraquinone is stirred in 70 ml of dioxane at 75° C. for 23 hours until the starting 1-fluoro-anthraquinone is consumed. The reaction mixture is then filtered and the residue taken up in ethyl acetate and successively washed with 1 N hydrogen chloride (3 times), saturated sodium hydrogen carbonate solution and brine. Evaporation of the solvent leaves the red compound of formula (9.3). $^1$H-NMR (CDCl$_3$, 300 MHz): 1.30-1.52 (m, 15H); 1.66-1.74 (m, 2H); 3.06 (broad q, 2H); 3.25 (dq, 2H); 4.45 (broad s, 1H); 6.97 (dd, 1H); 7.44 (dd, 1H); 7.50 (dd, 1H); 7.61 (dt, 1H); 7.67 (dd, 1H); 8.14 (m, 2H); 9.64 (broad t, 1H). $^{13}$C-NMR (CDCl$_3$, 75 MHz): 26.89; 27.23; 28.80; 29.39; 30.40; 40.08; 43.20; 79.78; 111.84;

115.77; 118.03; 126.85; 126.88; 133.04; 133.13; 134.07; 134.84; 135.18; 135.45; 151.08; 184.00; 184.59.

For Example 10

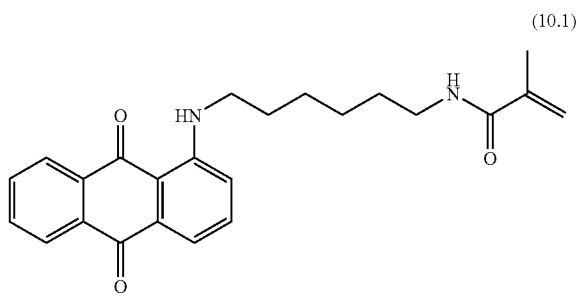

(10.1)

In analogy to the synthesis of compound 9.1, 5.20 g of the amine of formula (9.2) are converted to the amide of formula (10.1) with 2.10 ml of methacrylic acid chloride. The compound of formula (10.1) is purified over a short silica gel (230-400 mesh, FLUKA) column with hexane-ethyl acetate 1:1 (v/v). $^1$H-NMR (CDCl$_3$, 300 MHz): 1.20-1.83 (m, 8H); 1.96 (dd, 3H); 3.33 (dt, 2H); 5.29 (quint., 1H); 5.65 (quint., 1H); 5.85 (broad, 1H); 7.05 (dd, 1H); 7.52 (dd, 1H); 7.47 (dd, 1H); 7.57 (dd, 1H); 7.63 (dd, 1H); 7.74 (dd, 1H); 8.24 (m, 2H); 9.71 (broad t, 1H). $^{13}$C-NMR (CDCl$_3$, 75 MHz): 19.09; 27.03; 27.21; 29.34; 29.91; 39.91; 43.17; 113.10; 115.78; 118.03; 119.25; 126.83; 126.88; 133.06; 133.22; 134.07; 134.85; 135.22; 135.46; 140.48; 151.91; 168.55; 183.88; 185.07.

For Example 11

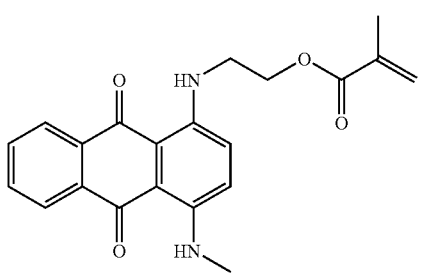

(11.1)

In analogy to the synthesis of compound 6.1, 0.25 g of the compound of formula (11.2) are esterfied with 1.00 ml methacrylic acid methylester and 0.5 g biocatalyst in 5 ml toluene at 60° C. to give the blue ester of formula (11.1) after a silica gel column (230-400 mesh, FLUKA) with eluent ethyl acetate. $^1$H-NMR (CDCl$_3$, 300 MHz): 1.96 (dd, 3H); 2.89 (d, 3H); 3.53 (dt, 2H); 4.32 (t, 2H); 5.55 (dq, 1H); 6.14 (dq, 1H); 6.90 (d, 1H); 7.00 (d, 1H); 7.75 (m, 2H); 8.18 (m, 2H); 10.32 (broad q, 1H); 10.61 (broad t, 1H). $^{13}$C-NMR (CDCl$_3$, 75 MHz): 18.69; 29.66; 41.63; 63.45; 110.06; 110.54; 122.75; 122.99; 126.07; 126.15; 126.40; 131.96; 132.11; 134.42; 134.56; 136.10; 145.37; 146.85; 167.33; 182.15; 182.61.

Compound 11.2:

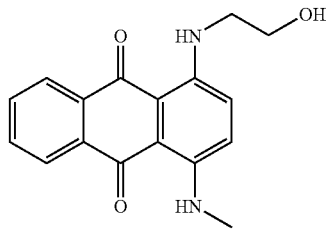

(11.2)

1-N-methyl-4-bromo anthraquinone (5.0 g), 2.0 ml of ethanolamine (FLUKA), 0.1 g of copper powder and 1.8 g of sodium acetate are given into 15 ml of toluene and heated to 80° C. with vigorous stirring. After 3 hours the mixture is applied to a silica gel (230-400 mesh, FLUKA) column and eluted with dichloromethane-methanol 10:1 (v/v) to give the desired alcohol of formula (11.2). $^1$H-NMR (CDCl$_3$, 300 MHz): 3.01 (s, 3H); 3.52 (t, 2H); 3.88 (t, 2H); 7.08 (d, 1H); 7.18 (d, 1H); 7.57 (m, 2v H); 8.22 (m, 2H); 10.48 (broad, 1H); 10.74 (broad, 1H). $^{13}$C-NMR (S(O)(CD$_3$)$_2$, 75 MHz): 30.00; 45.53; 60.71; 109.06; 109.11; 124.54; 125.25; 126.22; 126.26; 132.73 (2×C); 134.47; 134.51; 146.62; 147.28; 181.06 (2×C).

For Example 12

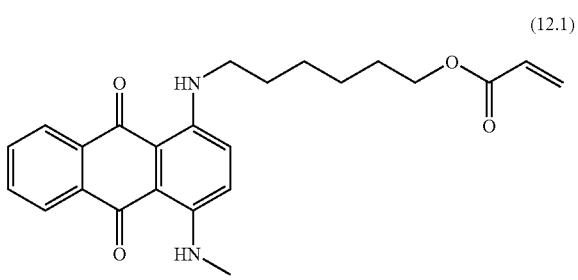

(12.1)

In analogy to the synthesis of compound 6.1, 5.0 g of the alcohol of formula (12.2) are converted to the ester of formula (12.1) in the presence of 4.0 g of biocatalyst. The ester of formula (12.1) is obtained after filtration from the catalyst and washing the biocatalyst with dichloromethane. $^1$H-NMR (CDCl$_3$, 300 MHz): 1.35-1.76 (m, 8H); 3.02 (d, 3H); 3.32 (dt, 2H); 4.09 (t, 2H); 5.74 (dd, 1H); 6.04 (dd, 1H); 6.28 (dd, 1H); 7.15 (s, 2H); 7.61 (m, 2H); 8.23 (m, 2H); 10.53 (broad q, 1H); 10.66 (broad t, 1H). $^{13}$C-NMR (CDCl$_3$, 75 MHz):

Compound 12.2:

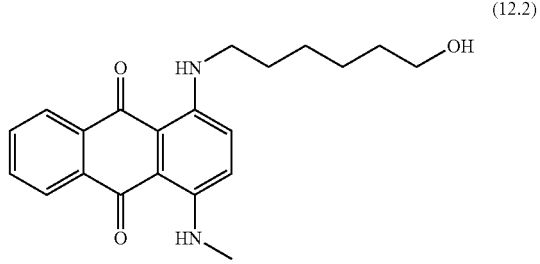

(12.2)

In analogy to the synthesis of compound 11.2, 1.0 g of 1-N-methyl-4-bromo anthraquinone, 1.0 g of 6-aminohexanol (FLUKA), 0.6 g of potassium carbonate and 0.2 g of copper powder are heated to 100° C. in 5 ml of toluene for 26 hours. The reaction mixture is filtered, washed with acetone and the residue dissolved in dichloromethane. The blue solution is applied to a silica gel (230-400 mesh, FLUKA) and eluted with dichloromethane-methanol 10:2 (v/v) to give 0.5 g of the desired blue alcohol of formula (12.2). $^1$H-NMR (CDCl$_3$, 300 MHz): 1.32-1.61 (m, 6H); 1.69 (quint., 2H); 2.99 (d, 3H); 3.29 (q, 2H); 3.58 (t, 2H); 7.10 (dd, 2H); 7.60 (dd, 2H); 8.21 (dd, 2H); 10.51 (broad, 1H); 10.64 (broad t, 1H). $^{13}$C-NMR (CDCl$_3$, 75 MHz): 25.86; 27.27; 29.83; 29.88; 32.95; 43.11; 63.04; 109.90; 110.09 123.24; 123.69; 126.17 (2×C); 132.10 (2×C); 134.03; 134.68; 146.34; 147.03; 182.35 (2×C).

For Example 13

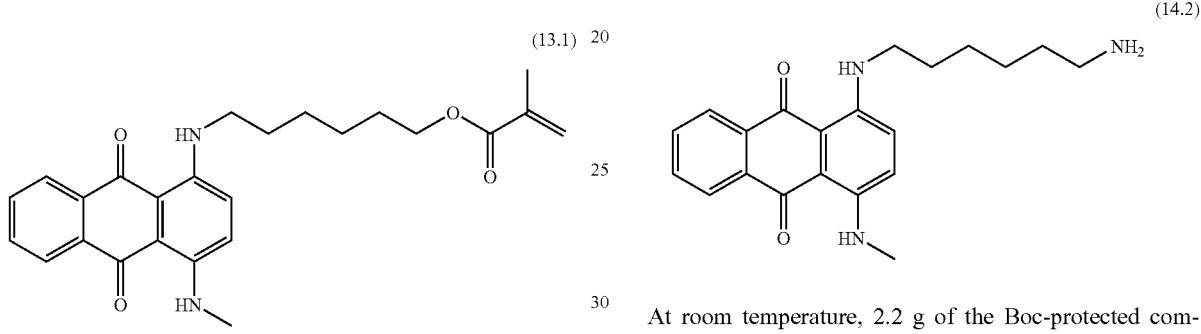

(13.1)

In analogy to the synthesis of compound 6.1, 1.7 g of the alcohol of formula (12.2) are converted to the ester of formula (13.1) in the presence of 2.5 g of biocatalyst. The ester of formula (13.1) is obtained after filtration from the catalyst and washing the biocatalyst with dichloromethane and a final purification over a silica gel (230-400 mesh, FLUKA) column (eluent: hexane-ethyl acetate 10:3 (v/v)). $^1$H-NMR (CDCl$_3$, 300 MHz): 1.37-1.52 (m, 4H); 1.60-1.77 (m, 4H); 1.87 (dd, 3H); 3.02 (s, 3H); 3.32 (dt, 2H); 4.08 (t, 2H); 5.45 (quint., 1H); 6.00 quint., 1H); 7.15 (m, 2H); 7.61 (m, 2H); 8.23 (m, 2H); 10.50 (broad, 1H); 10.70 (broad, 1H). $^{13}$C-NMR (CDCl$_3$, 75 MHz):

For Example 14

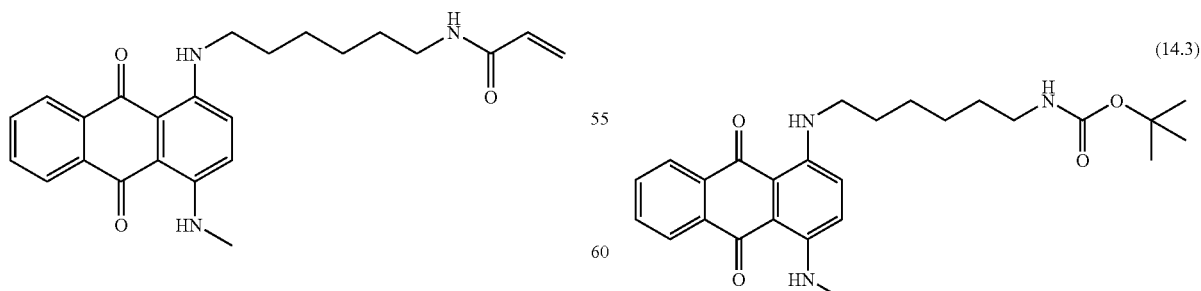

(14.1)

The compound of formula (14.2) (3.20 g) is dissolved together with 2.8 ml triethyl amine in 45 ml of dry dichloromethane at room temperature and then cooled down to −40° C. to −50° C. At this temperature 0.88 ml of acrylic acid chloride dissolved in 5 ml of dichloromethane are dropped into that mixture. After consumption of all the starting amine of formula (14.2), the organic phase is successively extracted with 1 N hydrogen chloride (3 times), a solution of saturated sodium hydrogen carbonate and brine. Evaporation of the organic phase leaves a blue residue which is purified over a silica gel (230-400 mesh, FLUKA) column with eluent dichloromethane-methanol 8:2 (v/v) to yield the amide of formula (14.1). $^1$H-NMR (CDCl$_3$, 300 MHz): 1.33-1.58 (m, 4H); 1.65-1.75 (m, 2H); 3.03 (s, 3H); 3.24-3.37 (m, 4H); 5.54 (dd, 1H); 5.60 (broad s, 1H); 6.00 (dd, 1H); 6.18 (dd, 1H); 7.17 (d, 2H); 7.58 (m, 2H); 8.23 (m, 2H); 10.56 (broad q, 1H); 10.68 (broad t, 1H). $^{13}$C-NMR (CDCl$_3$, 75 MHz): 26.94; 27.84; 29.72; 29.75; 29.84; 39.75; 42.93; 109.57; 109.75; 123.13; 123.51; 126.00; 126.08 (2×C); 128.97; 131.30; 131.93 (2×C); 134.54; 146.19; 146.91; 165.91; 182.32; 182.37.

Compound 14.2:

(14.2)

At room temperature, 2.2 g of the Boc-protected compound of formula (14.3) are dissolved in 5 ml of dioxane. To this mixture, then a solution of 10 ml 4 N hydrogen chloride in dioxane is added in small portions with vigorous stirring until the starting compound of formula (14.3) is consumed. The mixture is then evaporated and the resulting residue dissolved in water. The water phase is extracted with dichloromethane, then brought to pH=10 with a solution of 4 N sodium hydroxide, again extracted with dichloromethane and the organic phase dried with sodium sulphate to recover the desired blue amine. Evaporation of the solvent leaves the compound of formula (14.2). $^1$H-NMR (CDCl$_3$, 300 MHz): 1.31-1.52 (m, 4H); 1.68-1.77 (m, 2H); 2.68 (broad t, 2H); 3.02 (d, 3H); 3.30 (dq, 2H); 7.08 (d, 2H); 7.60-7.65 (m, 2H); 8.27 (m, 2H); 10.53 (broad q, 1H); 10.65 (broad t, 1H). $^{13}$C-NMR (CDCl$_3$, 75 MHz): 27.03; 27.44; 29.78; 29.98; 34.07; 42.49; 43.16; 109.82; 110.04; 123.08; 123.60; 126.12; 131.95; 132.02; 134.63; 134.68; 146.22; 146.92; 153.08; 182.20; 182.24.

Compound 14.3:

(14.3)

1-N-methyl-4-bromo anthraquinone (11.0 g), 4.8 g potassium carbonate, 0.5 g copper powder and 8.3 g N-Boc-1,6-diaminohexane (ALFA AESAR) are given into 70 ml toluene and heated to 75° C. with vigorous stirring. After 2.5 days, another batch of 0.8 g protected diamine is added. After 3 another 0.5 days, a further batch of 1.0 g protected diamine is added and stirring is continued for further 24 hours. The mixture is filtered and the organic phase washed successively with 2N hydrogen chloride (2 times), a solution of saturated sodium hydrogen carbonate and brine. Evaporation of the solvent leaves the protected amine of formula (14.3) which is processed without further purification. $^1$H-NMR (CDCl$_3$, 300 MHz): 1.37-1.57 (m, 15H); 1.72-1.81 (m, 2H); 3.06-3.16 (m, 5H); 3.37 (dt, 2H); 4.60 (broad s, 1H); 7.20 (s, 2H); 7.64-7.69 (m, 2H); 8.32 (m, 2H); 10.60 (broad q, 1H); 10.72 (broad t, 1H). $^{13}$C-NMR (CDCl$_3$, 75 MHz): 26.88; 27.19; 28.81; 29.85; 29.90; 40.11; 43.12; 79.78; 109.96; 110.14; 123.24; 123.70; 126.20 (2×C); 132.12 (2×C); 134.68 (2×C); 146.31; 147.04; 153.08; 182.44 (2×C).

For Example 15

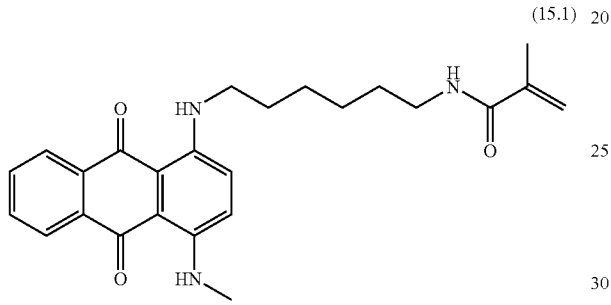

(15.1)

In analogy to the synthesis of compound 9.1, 3.50 g of the amine of formula (14.2) are converted to the amide of formula (15.1) with 1.7 ml of methacrylic acid chloride and 5.5 ml triethyl amine. After warming up to room temperature, the organic phase is successively extracted with 1 N hydrogen chloride (3 times), a solution of saturated sodium hydrogen carbonate and brine. The organic phase is dried over sodium sulphate and evaporated to give a blue residue which is purified over a silica gel (230-400 mesh, FLUKA) column with eluent ethyl acetate to yield the blue amide of formula (15.1). $^1$H-NMR (CDCl$_3$, 300 MHz): 1.36-1.62 (m, 6H); 1.71 (quint., 2H); 1.94 (dd, 3H); 3.02 (d, 3H); 3.29 (m, 4H); 5.26 (broad q, 1H); 5.64 (broad q, 1H); 6.01 (broad t, 1H); 7.08 (s, 2H); 7.64 (m, 2H); 8.26 (m, 2H); 10.54 (broad q, 1H); 10.65 (broad t, 1H). $^{13}$C-NMR (CDCl$_3$, 75 MHz): 19.09; 26.99; 27.1; 29.73; 29.77; 29.81; 39.89; 43.00; 109.72; 109.91; 119.28; 123.10; 123.54; 126.06; 126.10; 131.96 (2×C); 134.60; 134.61; 140.42; 146.17; 146.91; 168.62; 182.05 (2×C).

Example 16

Use for the Preparation of a Colored Foil

A dye according to any one of the preceding Examples 1 to 15 is added to the PE-LD melt for a foil in a ratio of 0.5% by weight. The mixture is extruded to provide a colored foil. Due to the nanostructure of the dye, advantageous properties of the colored foil result Example 17

Coloring of Wool

Wool is mordanted with KAl(SO$_4$)$_2$ (potassium alumn). A dye according to any one of the preceding Examples 1 to 15 is then added. The result is a colored wool which, due to the nanostructure of the dye, has advantageous properties.

The invention claimed is:
1. A colored compound of the general formula (I)

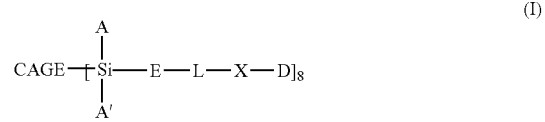

(I)

wherein
each of A and A' is, independently of the other, $C_1$-$C_4$ alkyl;
CAGE is a moiety of the formula IA

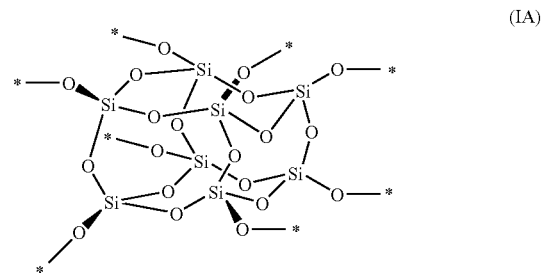

(IA)

wherein the asterisks (*) mark the bonds binding the moieties of the formula,

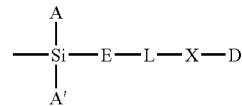

shown above, respectively,
D is a chromophoric unsubstituted or substituted anthraquinone moiety, with the proviso that all 8 moieties D in a molecule of the formula I are identical;
E is —C(R$_{3a}$)(R$_3$)—C(H)(R$_{3b}$)— and/or

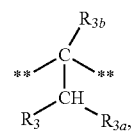

wherein the double asterisks (**) mark the binding bonds, respectively, and wherein each of R$_3$, R$_{3a}$ and R$_{3b}$, independently of the others, is hydrogen or unsubstituted or substituted $C_1$-$C_{12}$alkyl;
L is unsubstituted or substituted $C_1$-$C_{25}$alkylene which is linear or branched, which alkylene may be bound* and/or be interrupted by at least one of the radicals selected from the group consisting of —O—, —S—, —N(R$_4$)—, —CO—, —O—CO—, —CO—O—, —N(R$_4$)—CO—, —CO—N(R$_4$)— and phenylene, wherein R$_4$ is hydrogen or unsubstituted or substituted $C_1$-$C_{12}$alkyl;
X is —NR$_5$— or —O—; and
R$_5$ is hydrogen or unsubstituted or substituted $C_1$-$C_{12}$alkyl;
or a salt thereof.

2. A compound of the formula I according to claim 1, wherein D is an unsubstituted or substituted anthraquinone moiety selected from the group consisting of formula,

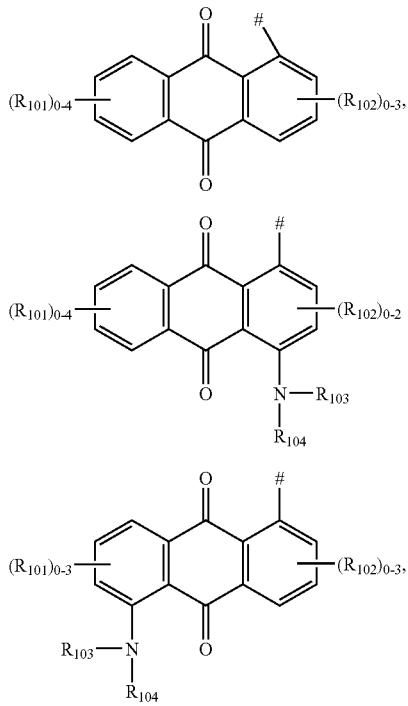

wherein the "#" sign marks the end of the bond that binds to X in formula I;
$R_{101}$ and $R_{102}$ are absent or are substitutents independently of each other selected from the group consisting of $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl, halogen, carboxyl, sulfo, sulfato, phosphono, phospho, cyano, nitro, amidino, ureido, carbamoyl, sulfamoyl, amino, $C_1$-$C_{10}$-alkanoylamino, mono- or di-($C_1$-$C_{12}$-alkyl)amino, a cationic quaternary ammonium or a cationic phosphonium group and from phenyl or benzoyl wherein phenyl or benzoyl is unsubstituted or substituted in the phenyl ring by at least one of the substituents just mentioned; and
$R_{103}$ and $R_{104}$ are independently selected from the group consisting of hydrogen, $C_1$-$C_{12}$-alkyl, hydroxyl-substituted $C_1$-$C_{12}$alkyl, and phenyl or phenyl-$C_1$-$C_{10}$alkyl, in both of which phenyl is unsubstituted or substituted by one or more moieties independently selected from $C_1$-$C_{12}$alkyl, hydroxyl-substituted $C_1$-$C_{12}$-alkyl, $C_1$-$C_{12}$alkoxy, hydroxyl-substituted $C_1$-$C_{12}$alkoxy, trifluoromethyl, hydroxyl fluoro, chloro, bromo, iodo, carboxyl, sulfo, sulfato, phosphono, phospho, cyano, nitro, amidino, ureido, carbamoyl, sulfamoyl, amino, $C_1$-$C_{10}$-alkanoylamino, mono- or di-($C_1$-$C_{12}$-alkyl)amino, and phenyl or benzoyl wherein phenyl or benzoyl is unsubstituted or substituted in the phenyl ring by at least one of the other substituents just mentioned;
and A, A', CAGE, E, L, $R_3$, $R_{3a}$, $R_{3b}$, $R_4$, X and $R_5$ are as defined in claim 1;
or a salt thereof.

3. A compound of the formula I according to claim 1, wherein D is a moiety of the formula

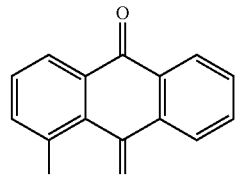

or a moiety of the formula

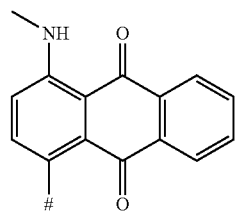

wherein the "#" sign marks the end of the bond that binds to X in formula I;
and n, A, A', CAGE, E, L, $R_3$, $R_{3a}$, $R_{3b}$, $R_4$, X and $R_5$ are as defined in claim 1;
or a salt thereof.

4. A compound of the formula I according to claim 1, wherein n is 8, each of A and A' is methyl,
CAGE is a moiety of the formula IA as shown in claim 1,
D is a moiety of the formula

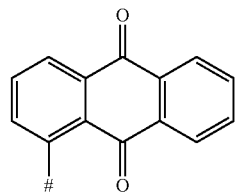

or a moiety of the formula

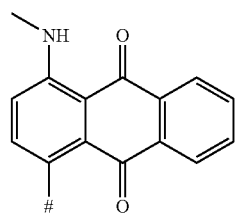

wherein the "#" sign marks the end of the bond that binds to X in formula I;
E is —C($R_3$)($R_3$)—C(H)($R_{3b}$)— and/or

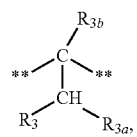

wherein the double asterisks (**) mark the binding bonds, respectively, and wherein each of $R_3$, $R_{3a}$ and $R_{3b}$ is hydrogen;

L is $C_1$-$C_{12}$-alkylene which is linear or branched which alkylene can be bound or interrupted by one or two of the radicals selected from the group consisting of phenylene, —CO—O— and —CO—NH—; and X is —NH— or —O—;

or a salt thereof.

5. A compound of the formula I according to claim 1, selected from the group consisting of

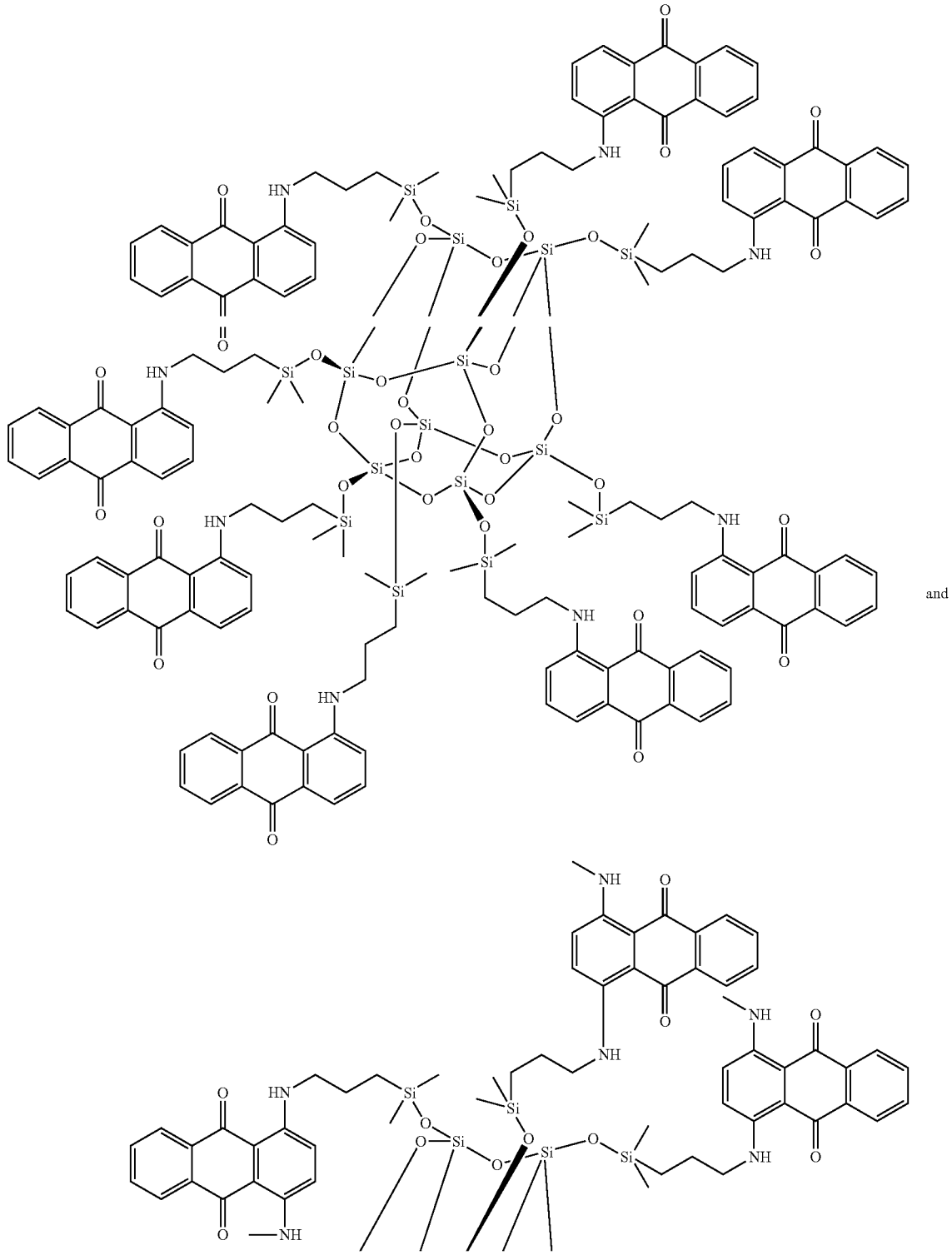

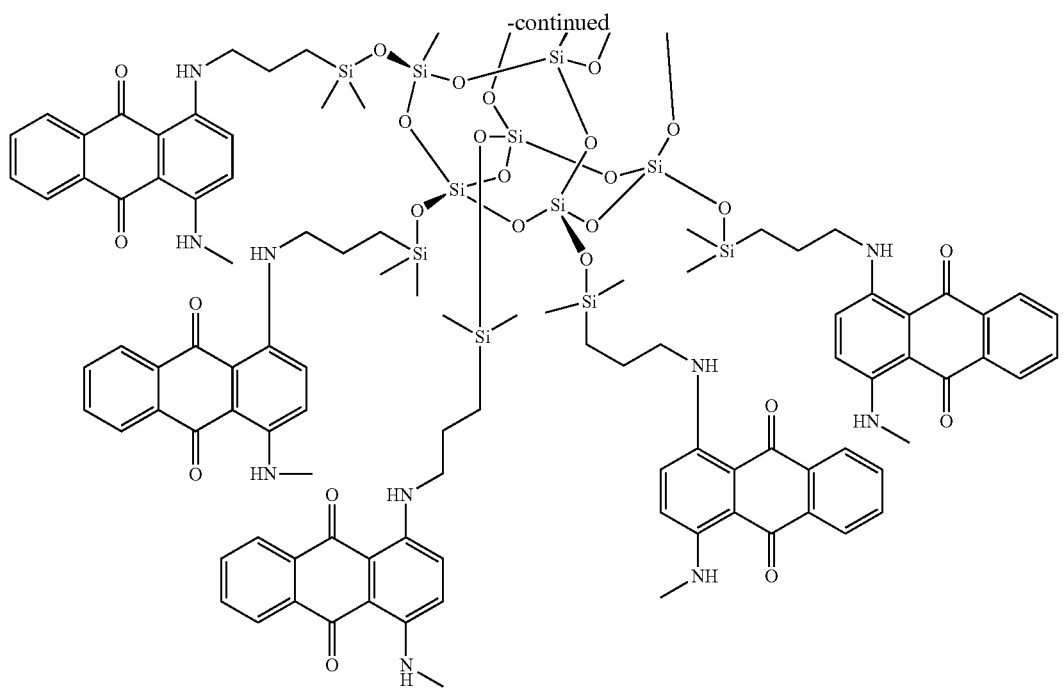
6. A compound of the formula I according to claim 1 wherein the moiety
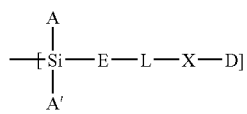
is selected from the group consisting of
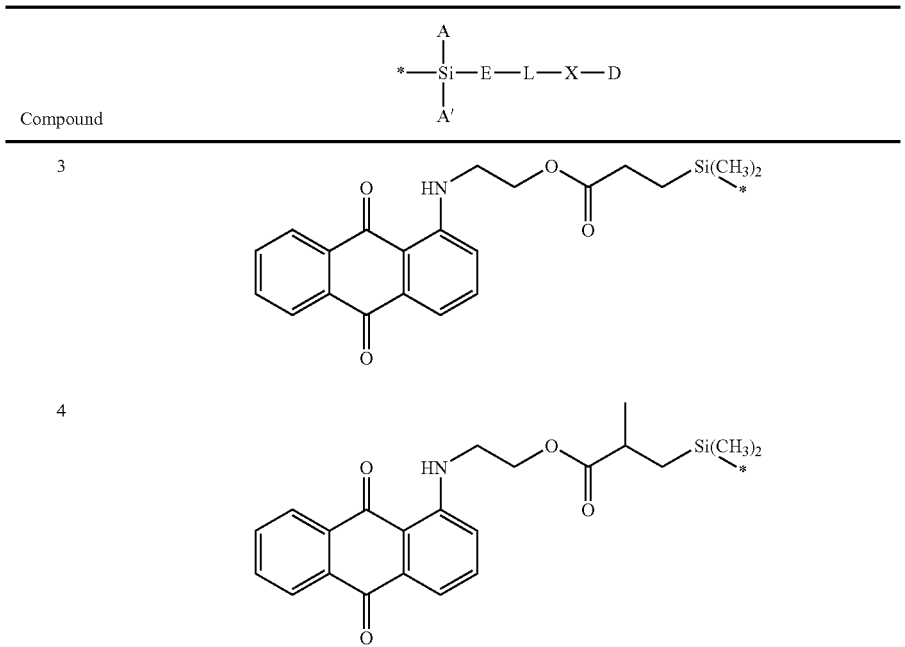

| Compound | $*\!-\!\underset{A'}{\overset{A}{Si}}\!-\!E\!-\!L\!-\!X\!-\!D$ |
|---|---|
| 5 | 1-[(2-{[4-(2-dimethylsilylethyl)benzoyl]oxy}ethyl)amino]anthracene-9,10-dione |
| 6 | 1-{[6-(3-dimethylsilylpropanoyloxy)hexyl]amino}anthracene-9,10-dione |
| 7 | 1-{[6-(2-methyl-3-dimethylsilylpropanoyloxy)hexyl]amino}anthracene-9,10-dione |
| 8 | 1-[(6-{[4-(2-dimethylsilylethyl)benzoyl]oxy}hexyl)amino]anthracene-9,10-dione |
| 9 | 1-{[6-(3-dimethylsilylpropanoylamino)hexyl]amino}anthracene-9,10-dione |

-continued
| Compound | $*\!\!-\!\!\underset{A'}{\overset{A}{Si}}\!\!-\!\!E\!\!-\!\!L\!\!-\!\!X\!\!-\!\!D$ |
|---|---|
| 10 | 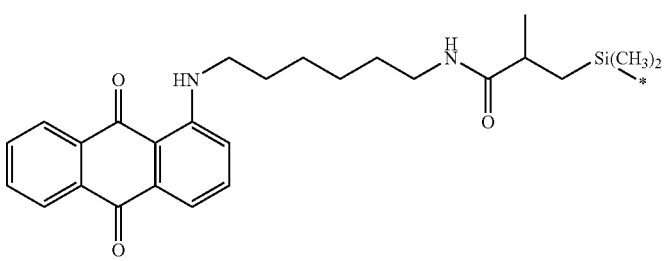 |
| 11 | 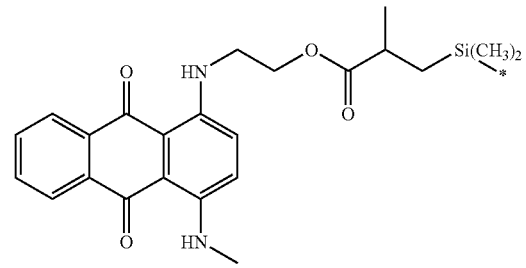 |
| 12 | 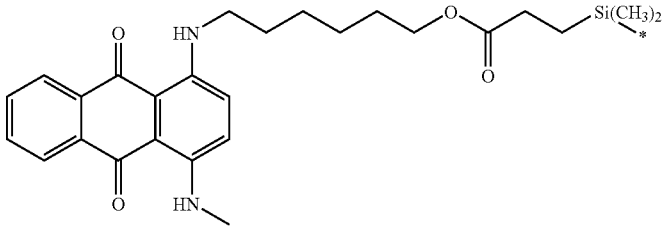 |
| 13 | 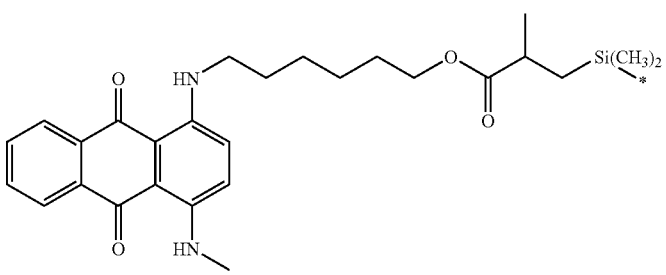 |
| 14 | 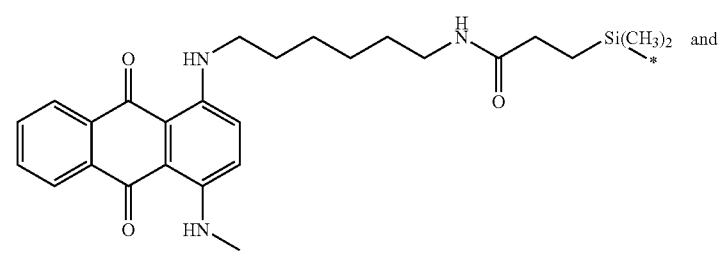 and |

-continued

| Compound | |
|---|---|
| | 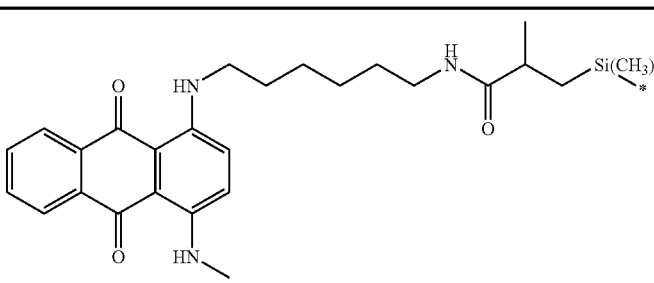 |
| 15 | |

7. A process for the manufacture of a compound of formula I according to claim 1,
wherein said process comprises
reacting a compound of the formula II,

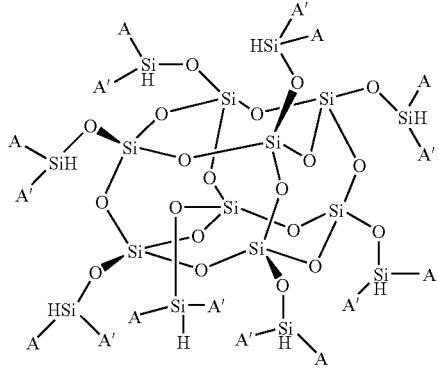

(II)

wherein A and A' are as defined for a compound of the formula I in claim 1,
under hydrosilylation conditions with a dye compound of the formula III,

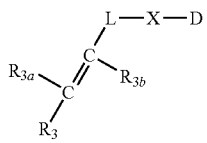

(III)

wherein $R_3$, $R_{3a}$, $R_{3b}$, L, X and D are as defined fro a compound of the formula I in claim 1;
wherein functional groups may be protected;
subsequently removing protecting groups;

and, optionally,
converting an obtainable free compound of the formula I into a salt, and/or an obtainable salt of a compound of the formula I into the free compound or into a different salt thereof; and/or
separating an obtainable isomer of a compound of the formula I from another obtainable isomer of a compound of the formula I.

8. A method of coloring a substrate wherein said method comprises applying to said substrate a tinctorially effective amount of a compound of the formula I according to claim 1, or a mixture of compounds of the formula I, in free form and/or as a salt, alone or in the form of a composition.

9. The method according to claim 8, wherein the substrate is selected from the group consisting of materials, goods, formulations, natural substrates, packages, labels and tags.

10. The method according to claim 8 wherein the compound of the formula I and/or a salt thereof, a mixture of such compound(s) and/or salt(s) and/or a composition comprising such compound(s) and/or salt(s) are applied to the outer surface, the inner surface and/or the bulk material of said substrate.

11. The compound of the formula I according to claim 1, wherein said D is substituted by one or more substituents, selected from the group consisting of $C_1$-$C_{10}$-alkyl, hydroxyl-, sulfo- and/or sulfato-substituted $C_1$-$C_{10}$-alkyl, $C_1$-$C_{10}$-alkoxy, hydroxyl-, sulfo- and/or sulfato-substituted $C_1$-$C_{10}$-alkoxy, trifluoromethyl, hydroxyl, halogen, carboxyl, sulfo, sulfato, phosphono, phospho, cyano, nitro, amidino, ureido, carbamoyl, sulfamoyl, amino, $C_1$-$C_{10}$-alkanoylamino, mono- or di-($C_1$-$C_{12}$-alkyl)amino, a cationic quaternary ammonium, and a cationic phosphonium and phenyl or benzoyl wherein phenyl or benzoyl is unsubstituted or substituted in the phenyl ring by at least one of the substituents just mentioned above.

12. The compound of the formula I according to claim 11, wherein phenyl or benzoyl is substituted in the phenyl ring by at least one of the substituents selected from the group consisting of $C_1$-$C_8$-alkyl, $C_1$-$C_8$-alkoxy, halogen and sulfo.

* * * * *